(12) United States Patent
Auclair et al.

(10) Patent No.: US 9,127,035 B2
(45) Date of Patent: Sep. 8, 2015

(54) COMPOUNDS FOR USE IN THE TREATMENT OF BACTERIAL INFECTION

(75) Inventors: Karine Auclair, Laval (CA); Kenward Vong, Toronto (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 9 days.

(21) Appl. No.: 13/980,364

(22) PCT Filed: Jan. 17, 2012

(86) PCT No.: PCT/CA2012/050029
§ 371 (c)(1),
(2), (4) Date: Oct. 1, 2013

(87) PCT Pub. No.: WO2012/097454
PCT Pub. Date: Jul. 26, 2012

(65) Prior Publication Data
US 2014/0038914 A1 Feb. 6, 2014

Related U.S. Application Data

(60) Provisional application No. 61/433,548, filed on Jan. 18, 2011.

(51) Int. Cl.
*A61K 31/70* (2006.01)
*C07H 15/224* (2006.01)
*A61K 31/7036* (2006.01)
*A61K 45/06* (2006.01)
*C07H 15/23* (2006.01)
*C07H 15/234* (2006.01)

(52) U.S. Cl.
CPC .......... *C07H 15/224* (2013.01); *A61K 31/7036* (2013.01); *A61K 45/06* (2013.01); *C07H 15/23* (2013.01); *C07H 15/234* (2013.01)

(58) Field of Classification Search
CPC .. C07H 15/224; C07H 15/23; A61K 31/7036; A61K 45/06
See application file for complete search history.

(56) References Cited

U.S. PATENT DOCUMENTS 7,626,005 B2    12/2009    Auclair et al.

OTHER PUBLICATIONS

Agnelli, F. et al., Angew. Chem. Int. Ed. 2004, 43, 1562-1566.
Akinnusi et al., Bioorg Med Chem. 19(8). 2011. pp. 2696-2706.
Alper, P. B. et al., Tet. Lett. 1996, 37, 6029-6032.
Boehr, D. D. et al., Biochemistry. 2004, 43, 9846-9855.
Chou, C. H. et al., Org. Lett. 2004, 6, 585-588.
Coates, A. et al., Nat. Rev. (Drug Discovery) 2002, 1, 895-910.
Culebras, E. et al., Front. Biosci. 1999, 4, D1-D8.
Davies, J. et al., Trends Microbiol 1997, 5, 234.
Ding, Y.-L. et al., Angew. Chem. Int. Ed. 2003, 42, 3409-3412.
Ding, Y.-L. et al., Tet. Lett. 2000, 41, 4049-4052.
Draker, K.-A. et al., Biochemistry 2004, 43, 446-454.
Fourmy, D. et al., J. Mol. Biol. 1998, 277, 347-362.
Fourmy, D. et al., Science 1996, 274, 1367-1375.
Gao, F. et al., Angew Chem Int Ed 2005 44:6859-6862.
Gao, F. et al., J. Med Chem. 49(17). 2006. pp. 5273-5281.
Gao, F. et al., Bioorg Med Chem. 18(20). 2008. pp. 5518-5522.
Gao, F. et al., Chemistry. 15(9). 2009. pp. 2064-2070.
Greenberg, W. A. et al., J Biol Chem 1999, 274:27105-27111.
Haddad, J. et al., J. Am. Chem. Soc. 2002, 124, 3229-3237.
Hanessian, S. et al., Tetrahedron, 2001, 57, 3255-3265.
Hanessian, S. et al., Tetrahedron. 2003, 59, 983-993.
Kim, C. M. et al., J. Med. Chem. 2001, 44, 2479-2485.
Li, X.-Z. et al., J. Antimicrob. Chemother. 2003, 5, 803-811.
Magalhães et al., Biochemistry. 15;47(2). 2008. pp. 579-584.
Magnet, S. et al., Biochemistry. 2001, 40. 3700-3709.
Magnet, S. et al., Antimicrob. Agents Chemother. 2003, 47, 1577-1583.
Marmorstein, R., J. Mol. Biol. 2001, 311, 433-444.
Michael, K. et al., Bioorg. Med. Chem. Lett. 1999, 7, 1361-1371.
Nazi, I. et al., Anal Biochem, 2004, 324:100-105.
Park, W. K. C. et al., J. Am. Chem. Soc. 1996, 118, 10150-10155.
Poux, A. N. et al., Proc. Nat. Acad. Sci. 2002, 99, 14065-14070.
Recht, M. I. et al., The EMBO J. 1999, 18, 3133-3138.
Roestamadji, J. et al., Bioorg. Med. Chem. Lett. 1998, 8, 3483-3488.
Sagar, V. et al., Bioorg. Med. Chem.y 2004, 12, 3383-3390.
Seeberger, P. H. et al., Synlett. 2003, 9, 1323-1326.

(Continued)

*Primary Examiner* — Elli Peselev
(74) *Attorney, Agent, or Firm* — Norton Rose Fulbright Canada LLP

(57) ABSTRACT

This invention relates to a compound of Formula 1A:

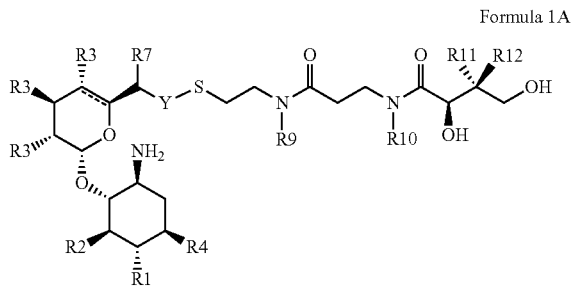

Formula 1A or a pharmaceutically acceptable salt thereof; wherein R1 to R4, R7, R9 to R12 and Y are as defined herein. The invention further relates to pharmaceutical composition comprising said compound or a pharmaceutically acceptable salt thereof; and method of using same for reducing or reversing bacterial resistance to at least one aminoglycoside antibiotic.

16 Claims, 6 Drawing Sheets

(56) References Cited

OTHER PUBLICATIONS

Strauss, E. et al., J Biol Chem. 2002, 277:48205-48209.
Tok, J. B.-H. et al., Curr. Topics Med. Chem. 2003, 3, 1001-1019.
Tok, J. B.-H. et al., Tetrahedron, 1999, 55, 5741-5748.
Vakulenko, S. B. et al., Clin. Microbiol. Rev. 2003, 16, 430-450.
Venot, A. et al., ChemBioChem 2004, 5, 1228-1236.
Verhelst, S. H. L. et al., J. Org. Chem. 2004, 2402-2410.
Vong, K. et al., Chemical Biology. 7(3). 2012. pp. 470-475.
Walsh, C., Nat. Rev. (Microbiology) 2003, 1, 65-70.
Williams, J. W. et al., J. Biol. Chem., 1978, 253: 5902-5907.
Williams, J. W. et al., J. Antibiotic 1979, 32, 1147-1154.
Worthington, A.-S. et al., Org Biomol Chem 2006, 4:44-46.
Wright, G. D. et al., Antimicrob. Agents Chemother. 1997, 41, 956-960.
Wright, G. D. et al., Resolving the Antibiotic Paradox, edited by Rosen and Mobashery, Kluwer Academic / Plenum Publishers, New York, 1998. p. 27-69.
Wybenga-Groot, L. E. et al., M. Structure 1999, 7, 497-507.
Yan et al., Bioorg Med Chem.. 15(8). 2007. pp. 2944-2951.
Yao, S.-L. et al., J. Bioorg. Med. Chem. Lett. 2004, 14, 3733-3738.
International Search Report of corresponding PCT application PCT/CA2012/050029.
Vong, K. et al, Med. Chem. Comm. 2012 vol. 3, No. 4, p. 397-407.
Supplementary European Search Report—EP 12736727.4 dated May 28, 2014.

COMPOUNDS FOR USE IN THE TREATMENT OF BACTERIAL INFECTION

CROSS-REFERENCE TO RELATED APPLICATION

This application incorporates by reference U.S. 61/433,548 filed Jan. 18, 2011 from which it claims priority.

FIELD OF THE INVENTION

The present invention relates to compounds and compositions comprising said compounds and their use in the treatment of bacterial infection.

BACKGROUND OF THE INVENTION

Aminoglycosides are among the most commonly used broad-spectrum antibiotics. They are often used clinically in combination with other antibiotics, such as β-lactams, as the first line of defense against serious infections caused particularly by various Gram-negative bacteria [(a) Wright, G. D.; Berghuis, A. M.; Mobashery, S. Resolving the Antibiotic Paradox, edited by Rosen and Mobashery, Kluwer Academic/Plenum Publishers, New York, 1998. p. 27-69. (b) Coates, A.; Hu, Y.-M.; Bax, R.; Page, C. Nat. Rev. (Drug Discovery) 2002, 1, 895-910. (c) Vakulenko, S. B.; Mobashery, S. Clin. Microbiol. Rev. 2003, 16, 430-450.]

Structurally, aminoglycosides often comprise a central 2-deoxystreptamine aminocyclitol ring to which amino sugars are linked through α-glycosidic bonds either at positions 4 and 5 (e.g. neomycin B) or at positions 4 and 6 as is the case for gentamicin $C_1$ and kanamycin A.

At physiological pH, the amino groups of aminoglycosides are protonated polycations. It is demonstrated that the main intracellular site of action of aminoglycosides is the ribosome, particularly the major groove of polyanionic 16S rRNA on the 30S ribosome of prokaryotic cells thereby disrupting protein biosynthesis. [(a) Recht, M. I.; Douthwaite, S.; Puglisi, J. D. The EMBO J. 1999, 18, 3133-3138. (b) Fourmy, D.; Recht, M. I.; Blanchard, S. C.; Puglisi, J. D. Science 1997, 274, 1367-1375. (c) Fourmy, D.; Recht, M. I.; Puglisi, J. D. J. Mol. Biol. 1998, 277, 347-362]. Inhibition of protein synthesis may not be the sole mechanism for the bactericidal activity of aminoglycoside antibiotics. For example, it is known that aminoglycosides displace cations noted for linking liposaccharides of Gram-negative bacteria.

The global emergence of bacterial resistance to aminoglycoside antibiotics is severely limiting widespread use. Bacterial resistance mitigates clinical efficacy in severe infections, thus creating a pressing need for the discovery and development of structurally novel and potent antibiotics against aminoglycoside-resistant strains. [Walsh, C. Nat. Rev. (Microbiology) 2003, 1, 65-70]. One approach to circumvent bacterial resistance is through derivatization of existing antibiotics [(a) Tok, J. B.-H.; Bi, L.-R. Curr. Topics Med. Chem. 2003, 3, 1001-1019 and references therein. (b) Seeberger, P. H.; Baumann, M.; Zhang, G.-T.; Kanemitsu, T.; Swayze, E. E.; Hofstadler, S. A.; Griffey, R. H. Synlett. 2003, 9, 1323-1326; [(a) Hanessian, S.; Tremblay, M.; Swayze, E. E. Tetrahedron. 2003, 59, 983-993. (b) Hanessian, S.; Tremblay, M.; Kornienko, A.; Moitessier, N. Tetrahedron, 2001, 57, 3255-3265. (c) Yao, S.-L.; Sgarbi, P. W. M.; Marby, K. A.; Rabuka, D.; O'Hare, S. M.; Cheng, M. L.; Bairi, M.; Hu, C.-Y.; Hwang, S.-B.; Hwang, C.-K.; Ichikawa, Y.; Sears, P.; Sucheck, S. J. Bioorg. Med. Chem. Lett. 2004, 14, 3733-3738. (d) Venot, A.; Swayze, E. E.; Griffey, R. H.; Boons, G.-J. Chem Bio Chem 2004, 5, 1228-1236.]

Derivatization of specific functional groups often prevents enzymatic inactivation of aminoglycosides without compromising antibacterial activity [Tok, J. B.-H.; Cho, J.-H.; Rando, R. R. Tetrahedron, 1999, 55, 5741-5748]. For example, dimerization of aminoglycosides has led to better activity against resistant strains [(a) Agnelli, F.; Sucheck, S. J.; Marby, K. A.; Rabuka, D.; Yao, S.-L.; Seras, P. S.; Liang, F.-S.; Wong, C.-H. Angew. Chem. Int. Ed. 2004, 43, 1562-1566. (b) Michael, K.; Wang, H.; Tor, Y. Bioorg. Med. Chem. Lett. 1999, 7, 1361-1371]. However, naturally occurring aminoglycosides are complex molecules and are often difficult to modify chemically. The judicious protection of functional groups is critical to selective derivatization, but is laborious [(a) Haddad, J.; Kotra, L. P.; Llano-Sotelo, B.; Kim, C.-K.; Azucena Jr, E. F.; Liu, M.-Z.; Vakulenko, S. B.; Chow, C. S.; Mobashery, S. J. Am. Chem. Soc. 2002, 124, 3229-3237. (b) Roestamadji, J.; Mobashery, S. Bioorg. Med. Chem. Lett. 1998, 8, 3483-3488]. Wong and others have developed a strategy based on the neamine scaffold and azido chemistry, to generate several neamine-based aminoglycoside analogs that exhibit good antibacterial activity against resistant strains [(a) Alper, P. B.; Huang, S.-C.; Wong, C.-H. Tet. Lett. 1996, 37, 6029-6032.; (b) Chou, C. H.; Wu, C. S.; Chen, C. H.; Lu, L. D.; Kulkarni, S. S.; Wong, C.-H. Huang, S. C. Org. Lett. 2004, 6, 585-588. (c) Greenberg, W. A.; Priestley, E. S.; Seras, P. S.; Aper, P. B.; Rosenbohm, C.; Hendrix, M.; Hung, S. C.; Wong, C.-H. J. Am, Chem. Soc., 1999, 121, 6527-6541. (d) Park, W. K. C.; Auer, M.; Jaksche, H.; Wong, C.-H. J. Am. Chem. Soc. 1996, 118, 10150-10155. (e) Ding, Y.-L.; Hofstadler, S. A.; Swayze, E. E.; Risen, L.; Griffey, R. H. Angew. Chem, Int. Ed. 2003, 42, 3409-3412. (f) Ding, Y.-L.; Swayze, E. E.; Hofstadler, S. A.; Griffey, R. H. Tet. Lett. 2000, 41, 4049-4052. (g) Verhelst, S. H. L.; Magnee, L.; Wennekes, T.; Wiedenhof, W.; van der Marel, G. A.; Overkleeft, H. S.; van Boeckel, C. A. A.; van Boom, J. H. Eur. J. Org. Chem. 2004, 2402-2410]. In spite of the recent advancements, regioselective modifications of aminoglycosides remain challenging. Chemically modified aminoglycosides may either be devoid of bactericidal activity or in other cases can have greater intrinsic toxicity. Chemically modified aminoglycosides are also more expensive to produce.

An alternative approach toward overcoming antibiotic resistance involves the suppression of the resistance-mediated processes. Inhibiting the enzymes responsible for causing drug resistance has proven to be a viable approach for overcoming bacterial resistance. For example the combination of a β-lactamase inhibitor (clavulinate) and a β-lactam antibiotic, has become front line therapy for fighting β-lactam resistant bacteria [(a) Draker, K-A.; Wright, G. D. Biochemistry 2004, 43, 446-454. (b) Draker, K.-A.; Northrop, D. B.; Wright, G. D. Biochemistry 2003, 42, 6565-6574].

The common mechanism associated with resistance to antimicrobial aminoglycosides is associated with bacterial expression of drug-modifying enzymes such as adenylyltransferases, phosphoryltransferases, and acetyltransferases [Davies, J.; Wright, G. D. Trends Microbiol 1997, 5, 234]. Among these, aminoglycoside 6'-N-acetyltransferases (AAC (6')s) are some of the most frequent drug modifying enzymes observed in clinical isolates. These enzymes exert their effect by transferring an acetyl group from acetyl coenzyme A (AcCoA) to the 6'-N of aminoglycosides thereby rendering the aminoglycoside ineffective as illustrated for kanamycin A.

In clinical isolates of aminoglycoside-resistant strains, N-acetyltransferase is one of the most frequently observed cause of resistance [(a) Wright, G. D.; Ladak, P. Antimicrob. Agents Chemother. 1997, 41, 956-960. (b) Boehr, D. D.; Daigle, D. M.; Wright, G. D. Biochemistry. 2004, 43, 9846-9855. (c) Culebras, E.; Martinez, J. L. Front. Biosci. 1999, 4, D1-D8. (d) Magnet, S.; Lambert, T.; Courvalin, P.; Blanchard, J. S. Biochemistry 2001, 40, 3700-3709. (e) Magnet, S.; Smith, T.-A.; Zheng, R.; Nordmann, P.; Blanchard, J. S. Antimicrob. Agents Chemother. 2003, 47, 1577-1583. (f) Li, X.-Z.; Zhang, L.; McKay, G. A.; Poole, K. J. Antimicrob. Chemother. 2003, 5, 803-811]. Examples of known AAC(6')s include, but are not limited to AAC(6')-Ii, AAC(6')-APH(2"), AAC(6')-Ie, AAC(6')-Iy, AAC(6')-29b, and AAC(6')-Iz.

Compounds characterized as bi-substrate analogues have been previously considered as potential inhibitors of, for example, serotonin acetyltransferase [Kim, C. M.; Cole, P. A. J. Med. Chem. 2001, 44, 2479-2485] and GCN5 histone acetyltransferase [(a) Poux, A. N.; Cebrat, M.; Kim, C. M.; Cole, P. A.; Marmorstein, R. Proc. Nat. Acad. Sci. 2002, 99, 14065-14070. (b) Sagar, V.; Zheng, W.-P.; Thompson, P.; Cole, P. A. Bioorg. Med. Chem.y 2004, 12, 3383-3390.]. Williams et al. have described the gentamicin acetyltransferase I-catalyzed transfer of a chloroacetyl group to generate exclusively 3-N-chloroacetylgentamicin. This derivative subsequently undergoes attack by the CoA thiol thus generated, to produce the bi-substrate analogs gentamicyl-3-N-acetyl CoA [Williams, J. W.; Northrop, D. B. J. Antibiotic 1979, 32, 1147-1154]. Gao et al. have reported first generation AAC(6')-Ii inhibitors that are bi-substrate analogs [Gao, F.; Yan, X.; Shakya, T.; Baettig, O. M.; Ait-Mohand-Brunet, S.; Berghuis, A. M.; Wright, G. D.; Auclair, K. J. Med. Chem, 2006, 49, 5273]. U.S. Pat. No. 7,626,005 teaches a class of aminoglycoside acetyltransferase inhibitors characterized as coenzyme A conjugated to the 6'-NH$_2$ of an aminoglycoside. However, these first generation AAC(6')-Ii inhibitors are charged high molecular weight species. There are limitations to the utility of charged high molecular weight compounds including but not limited to poor capacity or inability to permeate cell membranes, necessary to exert inhibition of aminoglycoside 6'-N-acetyltransferases.

There thus remains a need for inhibitors of aminoglycoside 6'-N-acetyltransferases. More specifically, there remains a need for inhibitors of aminoglycoside 6'-N-acetyltransferases capable of reversing or inhibiting bacterial resistance to aminoglycoside antibiotics. There further remains a need for compounds that permeate infected cells and inhibit aminoglycoside 6'-N-acetyltransferases intracellularly, thereby restoring efficacy of aminoglycoside antimicrobial agents.

Prodrugs are characterized as compounds that are pharmacologically inert but are activated in vivo by some biological mechanisms. Activation can take place for example enzymatically either extracellularly or intracellularly. Typically, the strategy to design prodrugs is often applied to overcome limitations relating to absorption, distribution, metabolism, and excretion.

The present description refers to a number of documents, the content of which is herein incorporated by reference in their entirety.

SUMMARY OF THE INVENTION

In one aspect of the disclosure, there is provided herein compounds of the formula (I) and analogs thereof; and pharmaceutically acceptable salts thereof:

R—Y—Z                                Formula I wherein:
R is selected from the group consisting of;

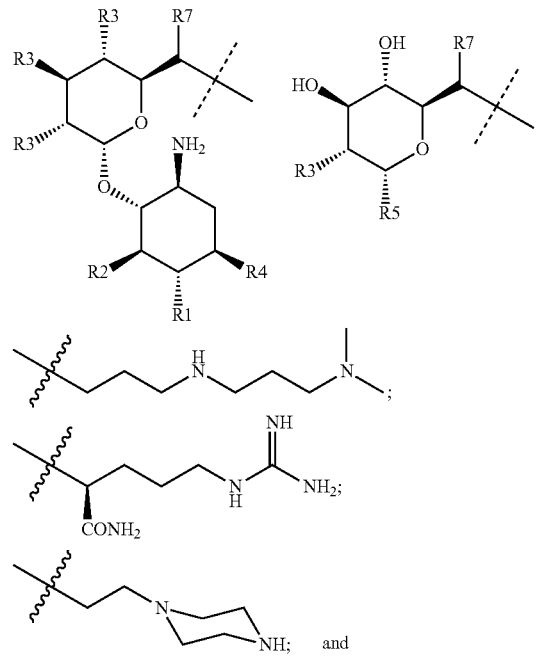

R7 is selected from the group consisting of H or CH$_3$;
R1 is selected from the group consisting of OH and

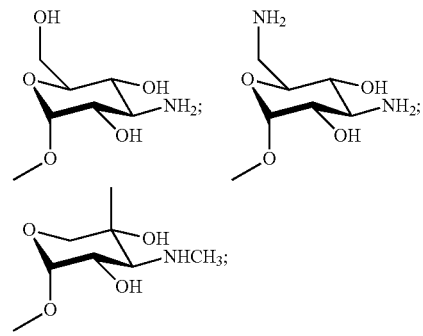

R2 is selected from the group consisting of OH and

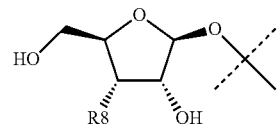

R8 is selected from a group consisting of OH and

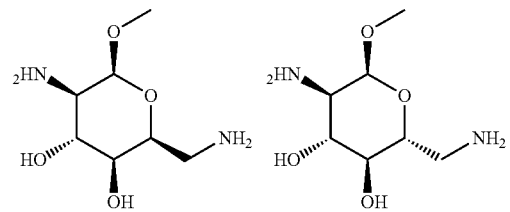

R3 is selected from the group consisting of H, NH$_2$ and OH;

R4 is selected from the group consisting of NH$_2$; and

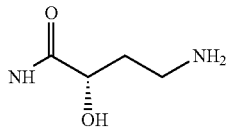

R5 is selected from the group consisting of OH, OMe, OEt OPr, and O-iPr;

Y is selected from the group consisting of:

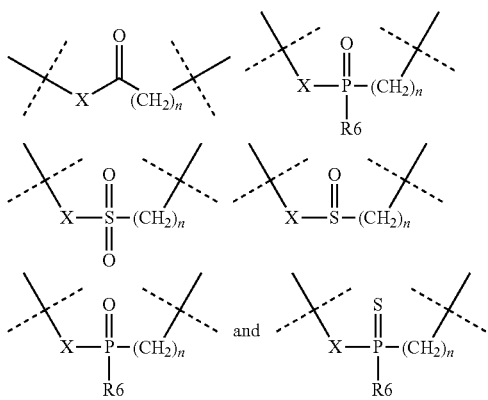

R6 is selected from the group consisting of OH, CH$_3$, and OCH$_3$;

X is selected from the group consisting of NH and O;

n is an integer ranging from 0 to 10;

Z is selected from the group consisting of:

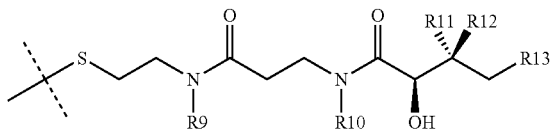

wherein R9, R10 and R11 and R12 are each independently selected from the group consisting of H, alkyl, alkenyl, cycloalkyl, heterocycloalkyl, cycloalkenyl, heterocycloalkenyl, aryl, or arylalkyl any of which may be optionally substituted; and R13 is OH or an acyloxy group and analogs thereof; and pharmaceutically acceptable salts thereof.

In one aspect of the disclosure, there is provided a pharmaceutical composition comprising at least one compound as defined herein and a pharmaceutically acceptable carrier, excipient and/or diluent.

In one aspect of the disclosure, there is provided a method for reducing or reversing bacterial resistance to at least one aminoglycoside antibiotics comprising administering a compound as defined herein or a pharmaceutically acceptable salt thereof.

In another aspect of the disclosure, there is provided a method for sensitizing or resensitizing a bacteria to a treatment with an aminoglycoside antibiotic comprising administering a compound as defined herein or a pharmaceutically acceptable salt thereof.

In a further aspect of the disclosure, there is provided a pharmaceutical composition as defined herein for use in combination with at least one aminoglycoside antibiotic for treating or preventing bacterial infection resistant to said at least one aminoglycoside antibiotic.

BRIEF DESCRIPTION OF THE DRAWINGS

Particular embodiments of the present invention will now be explained by way of example and with reference to the accompanying drawings, in which.

DETAILED DESCRIPTION OF THE PREFERRED EMBODIMENT

Figure 1:
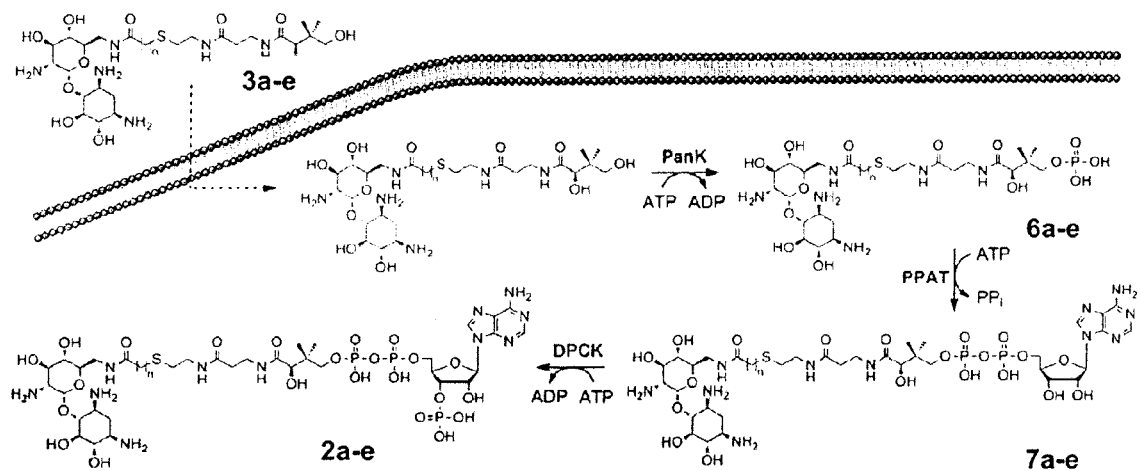
FIG. 1 shows a schematic of the enzymatic activation of the compounds of the invention. Following cell membrane penetration, 3a-e undergo phosphorylation by PanK to generate 6a-e, followed by PPAT-catalyzed adenylylation to 7a-e, and phosphorylation by DPCK to generate 2a-e.
Figure 2:
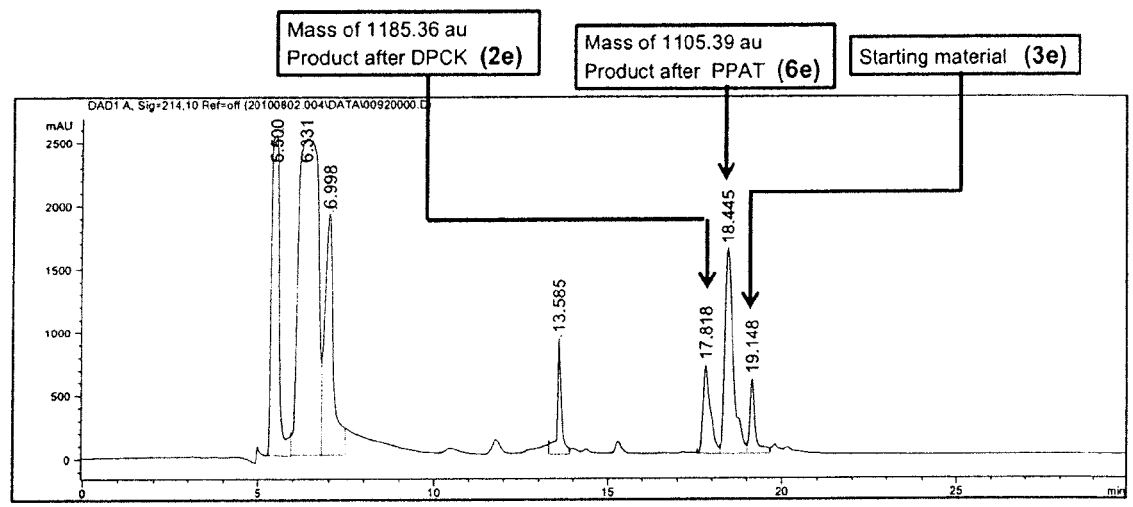
FIG. 2 shows HPLC chromatogram of the in vitro biosynthetic transformation of compound 3e by pantothenate kinase (PanK), phosphopantetheine adenylyltransferase (PPAT), and dephosphocoenzyme A kinase (DPCK); and identification by mass spectral analysis.

While the making and using of various embodiments are discussed below, it should be appreciated that the specific embodiments discussed herein are merely illustrative of specific ways of making and using the invention and should not be construed as to limit the scope of the invention.

In accordance with one embodiment, the disclosure provides a compound of Formula 1A:

Formula 1A

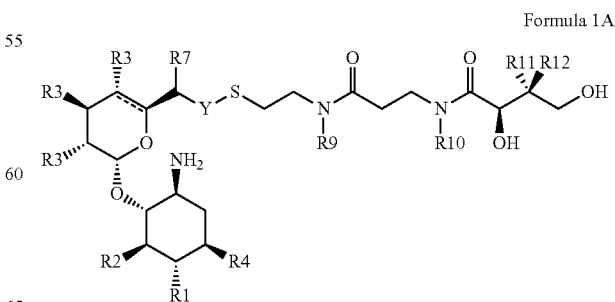

or a pharmaceutically acceptable salt thereof;

wherein the dotted line is an optional double bond;

R1 is selected from the group consisting of OH

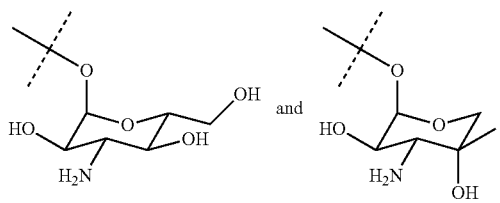

and

R2 is selected from the group consisting of OH and

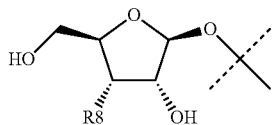

R3 is selected from the group consisting of H, NH$_2$ and OH;

R4 is selected from the group consisting of NH$_2$ and

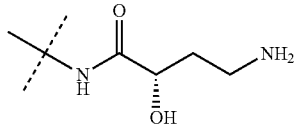

R7 is selected from the group consisting of H and CH$_3$;

R8 is selected from a group consisting of OH

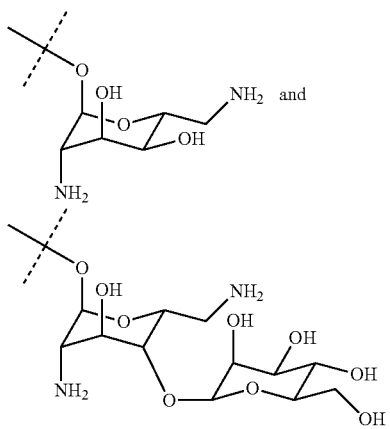

Y is selected from the group consisting of:

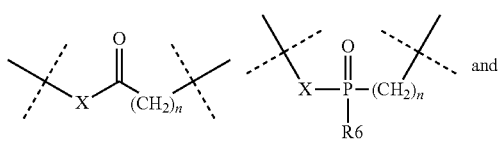

and

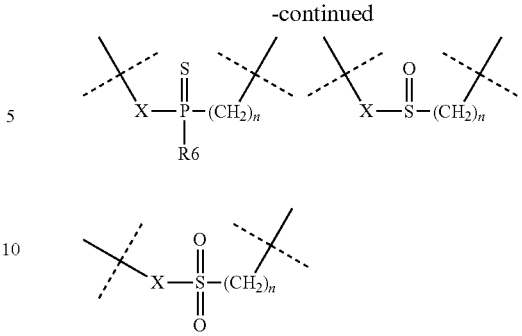

X is selected from the group consisting of NH and O;

R6 is selected from the group consisting of OH, CH$_3$, and OCH$_3$;

n is 0 or an integer from 2 to 5; and

R9, R10, R11 and R12 are each independently selected from the group consisting of H and C1-6 alkyl, provided that when the dotted line is a double bond, R3 of the residue

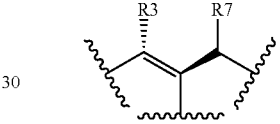

is H.

In accordance with one embodiment, the present disclosure provides a compound of Formula IIA and IIB

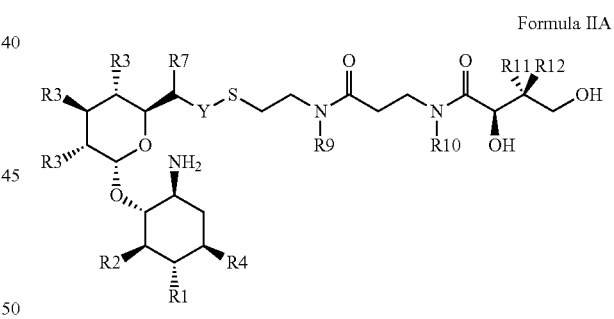

Formula IIA

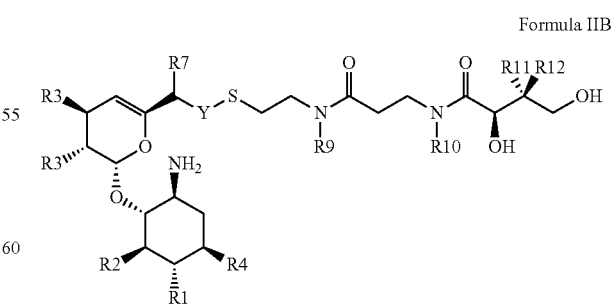

Formula IIB or a pharmaceutically acceptable salt thereof.

In accordance with one embodiment, the present disclosure provides a compound of Formula III

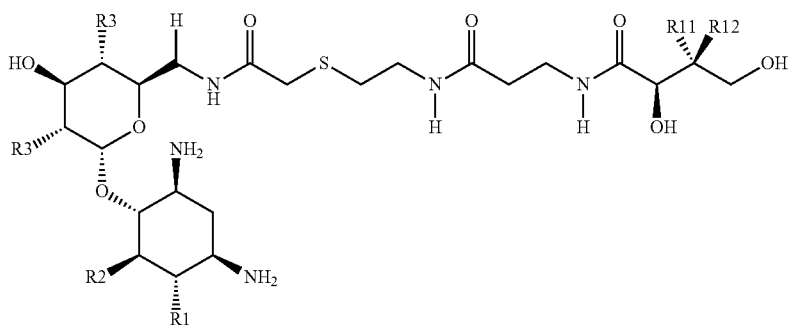

or a pharmaceutically acceptable salt thereof.

In accordance with one embodiment, the present disclosure provides a compound of Formula I, IA, IIA, IIB or III or a pharmaceutically acceptable salt thereof, wherein n is an integer from 2 to 5.

In accordance with one embodiment, the present disclosure provides a compound of Formula I, IA, IIA, IIB or III or a pharmaceutically acceptable salt thereof, wherein R1 is OH and R2 is OH.

In accordance with one embodiment, the present disclosure provides a compound of Formula I, IA, IIA, IIB or III or a pharmaceutically acceptable salt thereof, wherein R1 is OH and R2 is

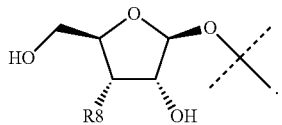

In accordance with one embodiment, the present disclosure provides a compound of Formula I, IA, IIA, IIB or III or a pharmaceutically acceptable salt thereof, wherein R1 is OH, R2 is

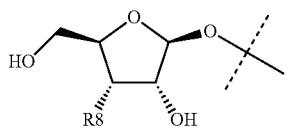

and R8 is OH.

In accordance with one embodiment, the present disclosure provides a compound of Formula I, IA, IIA, IIB or III or a pharmaceutically acceptable salt thereof, wherein R1 is OH, R2 is

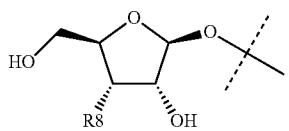

and R8 is selected from the group consisting of

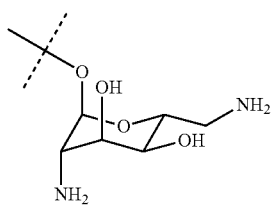

and

-continued

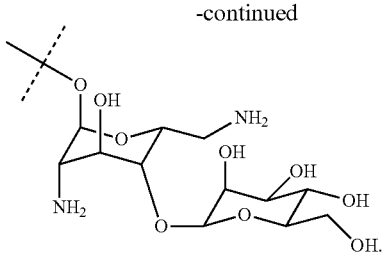

In accordance with another embodiment, the present disclosure provides a compound of Formula I, IA, IIA, IIB or III or a pharmaceutically acceptable salt thereof, wherein R1 is selected from the group consisting of

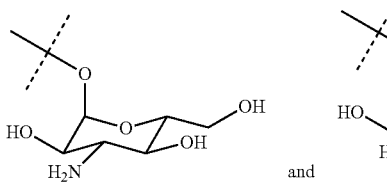 and 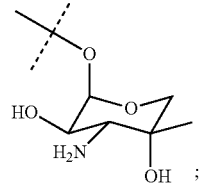 ;

and R2 is OH.

In accordance with another embodiment, the present disclosure provides a compound of Formula I, IA, IIA or IIB or a pharmaceutically acceptable salt thereof, wherein when one of R3 is $NH_2$, the others of R3 are OH or H.

In accordance with another embodiment, the present disclosure provides a compound of Formula I, IA, IIA, IIB or III or a pharmaceutically acceptable salt thereof, wherein Y is

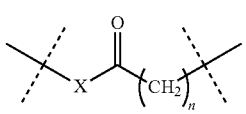

and X is NH.

In accordance with another embodiment, the present disclosure provides a compound of Formula I, IA, IIA or IIB or a pharmaceutically acceptable salt thereof, wherein R7 is H.

In accordance with another embodiment, the present disclosure provides a compound of Formula I, IA, IIA or IIB or a pharmaceutically acceptable salt thereof, wherein R4 is $NH_2$.

In accordance with another embodiment, the present disclosure provides a compound of Formula I, IA, IIA, IIB or III or a pharmaceutically acceptable salt thereof, wherein R11 and R12 are each independently C1-6 alkyl.

In accordance with another embodiment, the present disclosure provides a compound of Formula I, IA, IIA, IIB or III or a pharmaceutically acceptable salt thereof, wherein R9, R10, R11 and R12 are each independently selected from the group consisting of H and C1-3 alkyl, In accordance with another embodiment, the present disclosure provides a compound of Formula I, IA, IIA, IIB or III or a pharmaceutically acceptable salt thereof, wherein R9 and R10 are H and R11 and R12 are each independently C1-3alkyl.

In accordance with another embodiment, the present disclosure provides a compound of Formula I, IA, IIA or IIB or a pharmaceutically acceptable salt thereof, wherein R1 and R2 are as defined above, when one of R3 is NH$_2$, the others of R3 are OH or H, Y is

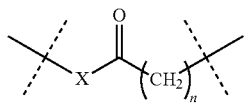

and X is NH.

In accordance with another embodiment, the present disclosure provides a compound of Formula I, IA, IIA or IIB or a pharmaceutically acceptable salt thereof, wherein R1 and R2 are as defined above, when one of R3 is NH$_2$, the others of R3 are OH or H, Y is

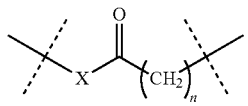

X is NH and n is an integer from 2 to 5.

In accordance with another embodiment, the present disclosure provides a compound of Formula I, IA, IIA or IIB or a pharmaceutically acceptable salt thereof, wherein R1 and R2 are as defined above, when one of R3 is NH$_2$, the others of R3 are OH or H, R7 is H, Y is

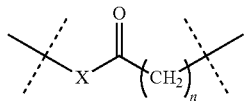

and X is NH.

In accordance with another embodiment, the present disclosure provides a compound of Formula I, IA, IIA or IIB or a pharmaceutically acceptable salt thereof, wherein R1 and R2 are as defined above, when one of R3 is NH$_2$, the others of R3 are OH or H, R7 is H, Y is

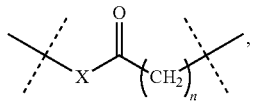

X is NH and n is an integer from 2 to 5.

In accordance with another embodiment, the present disclosure provides a compound of Formula I, IA, IIA or IIB or a pharmaceutically acceptable salt thereof, wherein R1 and R2 are as defined above, when one of R3 is NH$_2$, the others of R3 are OH or H, R4 is NH$_2$, R7 is H, Y is

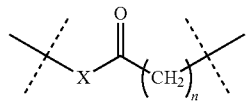

and X is NH.

In accordance with another embodiment, the present disclosure provides a compound of Formula I, IA, IIA or IIB or a pharmaceutically acceptable salt thereof, wherein R1 and R2 are as defined above, when one of R3 is NH$_2$, the others of R3 are OH or H, R4 is NH$_2$, R7 is H, Y is

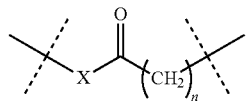

X is NH, R9 and R10 are H and R11 and R12 are each independently C1-3 alkyl.

In accordance with another embodiment, the present disclosure provides a compound of Formula I, IA, IIA or IIB or a pharmaceutically acceptable salt thereof, wherein R1, R2 are as defined above, when one of R3 is NH$_2$, the others of R3 are OH or H, R4 is NH$_2$, R7 is H, Y is

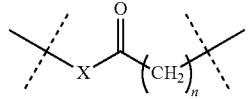

X is NH, n is an integer from 2 to 5, R9 and R10 are H and R11 and R12 are each independently C1-3 alkyl.

In accordance with another embodiment, the present disclosure provides a compound of Formula I, IA, IIA, IIB or III or a pharmaceutically acceptable salt thereof, wherein R11 and R12 are each independently C1-3 alkyl.

In accordance with another embodiment, the present disclosure provides a compound of Formula I, IA, IIA, IIB or III or a pharmaceutically acceptable salt thereof, wherein R11 and R12 are each methyl.

In accordance with another embodiment, the present disclosure provides a compound of Formula I, IA, IIA, IIB or III or a pharmaceutically acceptable salt thereof, wherein $R_{12}$=CH$_3$; $R_{11}$=CH$_3$; $R_{12}$=CH$_3$, $R_{11}$=CH$_2$CH$_3$; $R_{12}$=CH$_3$, $R_{11}$=CH$_2$CH$_2$CH$_3$; $R_{12}$=CH$_3$, $R_{11}$=CH$_2$(CH$_2$)$_4$CH$_3$; $R_{12}$=CH$_3$, $R_{11}$=CH$_2$CH=CH$_2$; $R_{12}$=CH$_3$, $R_{11}$=CH$_2$C$_6$H$_6$; $R_{12}$=CH$_3$, $R_{11}$=CH(CH$_3$)$_2$; $R_{12}$=CH$_2$CH$_2$CH$_3$, $R_{11}$=CH$_2$CH$_2$CH$_3$; $R_{12}$=CH$_2$CH=CH$_2$, $R_{11}$=CH$_2$CH=CH$_2$; $R_{12}$=CH$_3$, $R_{11}$=Cyclopropyl; $R_{12}$=CH$_3$, $R_{11}$=Cyclobutyl.

In another embodiment, there is provided herein a compound having the structure of formula 3a:

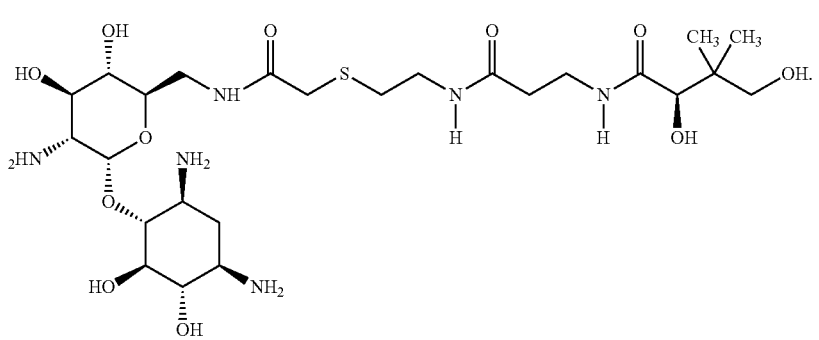
3a
In another embodiment, there is provided herein a compound having the structure of formula 3b:
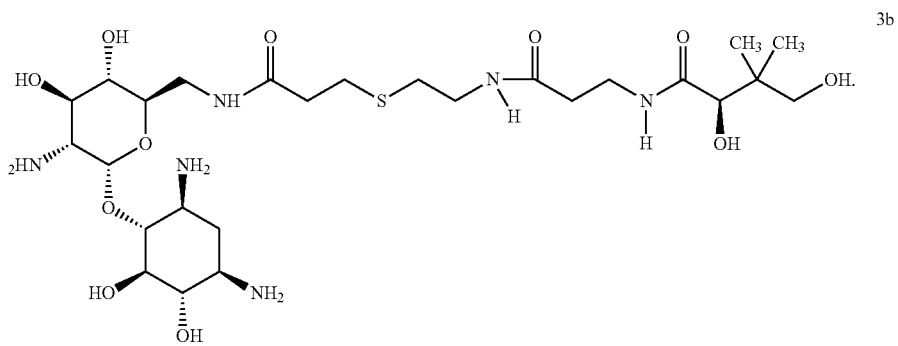
3b
In another embodiment, there is provided herein a compound having the structure of formula 3c:
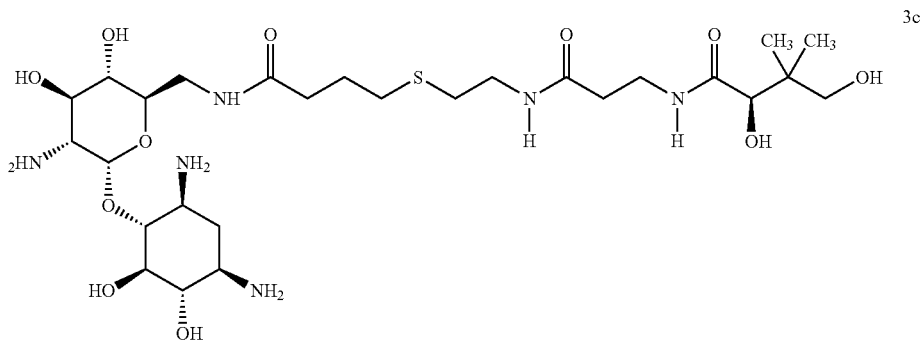
3c
In another embodiment, there is provided herein a compound having the structure of formula 3d:
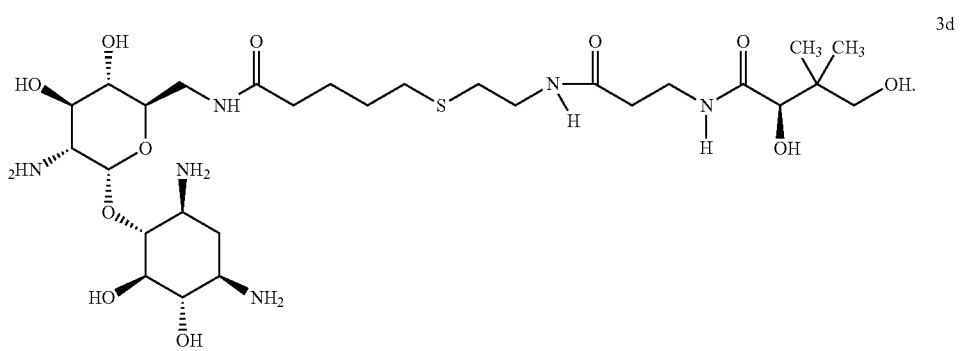
3d In another embodiment, there is provided herein a compound having the structure of formula 3e:

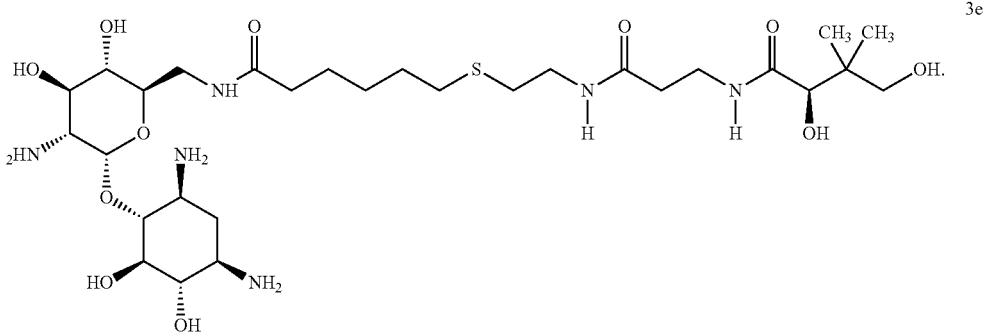

In another embodiment, there is provided herein a compound having the structure of formula 3f:

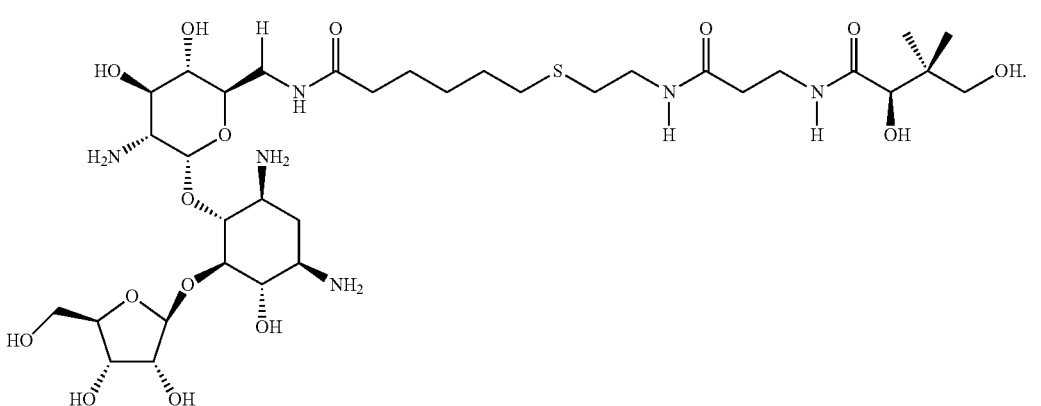

In another embodiment, there is provided herein a compound having the structure of formula 3g:

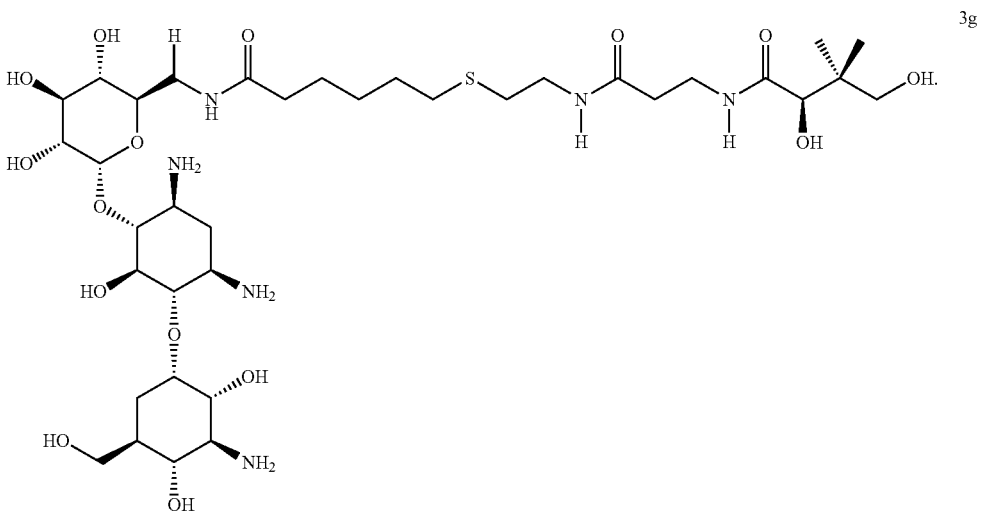

The term "alkyl group", as used herein, is understood as referring to a saturated, monovalent unbranched or branched hydrocarbon chain. Examples of alkyl groups include, but are not limited to, C1-6 alkyl groups. In another embodiment, the alkyl group includes C1-3 alkyl group. Examples of C1-6 alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, nonyl and decyl.

The term "analog" is intended to mean a compound that is similar or comparable, but not identical, to a reference compound, i.e. a compound similar in function, structure, properties and/or appearance to the reference compound. For example, the reference compound can be a reference green tea polyphenol and an analog is a substance possessing a chemical structure or chemical properties similar to those of the reference green tea polyphenol. As used herein, an analog is a chemical compound that may be structurally related to another but differs in composition (for example as in the replacement of one atom by an atom of a different element or in the presence of a particular functional group). An analog may be derived from a natural source or be prepared using chemical synthesis.

The term "acyl group" is intended to mean a group having the formula RC═O, wherein R is an alkyl, alkenyl, cycloalkyl, heterocycloalkyl, cycloalkenyl, heterocycloalkenyl, or an aryl group.

The term "aryl", as used herein, is understood as referring to 5-, 6- and 7- or more membered aromatic groups, for example phenyl or naphthyl, that may include from zero to four heteroatoms selected independently from O, N and S in the ring, for example, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaryl". The aromatic ring can be substituted at one or more ring positions. Aryl groups can also be part of a polycyclic group. For example, aryl groups include fused aromatic moieties such as naphthyl, anthracenyl, quinolyl, indolyl, and the like.

The term "alkenyl" refers to a straight or branched chain alkyl moiety having two or more carbon atoms (e.g., two to six carbon atoms, C2-6 alkenyl) and having in addition one double bond, of either E or Z stereochemistry where applicable. This term would include, for example, vinyl, 1-propenyl, 1- and 2-butenyl, 2-methyl-2-propenyl, etc.

The term "cycloalkyl" refers to a saturated alicyclic moiety having three or more carbon atoms (e.g., from three to six carbon atoms) and which may be optionally benzofused at any available position. This term includes, for example, cyclopropyl, cyclobutyl, cyclopentyl, cyclohexyl, indanyl and tetrahydronaphthyl.

The term "cycloalkenyl" refers to an alicyclic moiety having three or more carbon atoms (e.g., from three to six carbon atoms) and having in addition one double bond. This term includes, for example, cyclopentenyl or cyclohexenyl.

The term "heterocycloalkyl" refers to a saturated heterocyclic moiety having three or more carbon atoms (e.g., from three to six carbon atoms) and one or more heteroatoms from the group N, O, S (or oxidised versions thereof) and which may be optionally benzofused at any available position. This term includes, for example, azetidinyl, pyrrolidinyl, tetrahydrofuranyl, piperidinyl, indolinyl and tetrahydroquinolinyl.

The term "optionally substituted" means optionally substituted with one or more of the aforementioned groups (e.g., alkyl, aryl, heteroaryl, acyl, alkenyl, cycloalkyl, heterocycloalkyl, cycloalkenyl, heterocycloalkenyl, or halogen), at any available position or positions.

The present disclosure further relates to the method of using a compound described herein or a pharmaceutically acceptable salt thereof and composition comprising said compound for reducing or reversing bacterial resistance to at least one aminoglycoside antibiotic. The compound described herein possesses physical properties which allows to permeate the infected cells. Then, as explained above, the compound may undergo intracellular biotransformation thereby rendering said compound capable of inhibiting of 6'-N-acetyltransferases intracellularly. This enzymatic inhibition results in sensitization or resensitization of the bacteria to aminoglycoside antibiotics. Therefore, the compound can potentialize the aminoglycoside antibiotics against a resistant strain.

The present disclosure further relates to the method of using the compounds described herein wherein the bacteria comprises aminoglycoside 6'-N-acetyltransferase.

In one embodiment, the bacterial infection comprises AAC (6')-expressing resistant strains, more particularly the AAC (6')-expressing resistant strains may be AAC(6')-li- or AAC (6)-ly-expressing resistant strains.

In one embodiment, there is provided a pharmaceutical composition comprising at least one compound as defined herein or a pharmaceutically acceptable salt thereof, in association with one or more pharmaceutically acceptable carriers, excipients or diluents.

In one embodiment, the compound or pharmaceutical composition comprising said compounds can be further used in combination with at least one additional active ingredient or therapeutic agent. For example, the pharmaceutical compositions may further comprise a second therapeutic agent which is an aminoglycoside antibiotic including, without limitation, amikacin, gentamicin; kanamycin; neomycin; netilmicin; streptomycin, tobramycin, ribostamycin, ciprofloxacin and trovafloxacin.

The compound defined herein or the pharmaceutical composition comprising said compound may be used in combination with at least one aminoglycoside antibiotic, wherein both the compound or composition and said aminoglycoside antibiotics are for simultaneous or sequential administration.

In another embodiment, there is provided a pharmaceutical composition as described herein for use in combination with at least one aminoglycoside antibiotic for treating or preventing bacterial infection resistant to said at least one aminoglycoside antibiotic.

The present invention further relates to compounds, compositions and methods of use thereof for the treatment of microbial resistance. More specifically, but not exclusively, the present invention relates to compounds and compositions that are metabolically activated into inhibitors of aminoglycoside 6'-N-acetyltransferases, thereby, resistant cells become chemosensitive to aminoglycoside antibiotics.

In one embodiment, the present invention relates to compounds and compositions that undergo metabolic transformation into inhibitors of AAC(6')-li and AAC(6')ly).

In a further embodiment, the present invention relates to synthetic methodologies for preparing the compounds and compositions of the invention.

In one embodiment, the present invention relates to a use of a compound of the invention as defined herein, for the manufacture of a medicament for treating or preventing a disease or condition associated with bacterial resistance to aminoglycoside antibiotics.

Also provided herein are methods for inhibiting an aminoglycoside 6'-N-acetyltransferases in a cell, comprising contacting the cell with an effective amount of at least one compound or pharmaceutical composition of the invention, such that the said aminoglycoside 6'-N-acetyltransferases in the cell are inhibited upon the compounds of the invention undergoing biotransformation to the active ingredient. The contacting may occur in vitro or in vivo. Compounds and compositions may be administered by a variety of routes, such as orally, parenterally, subcutaneously, intravenously, intramuscularly, intraperitoneally, intraarterially, transdermally, and via mucosal administration.

In one embodiment, there is provided herein a pharmaceutical composition comprising a pharmaceutically effective amount of one or more compounds of the invention as defined herein, or pharmaceutically acceptable salts thereof, in association with one or more pharmaceutically acceptable carriers. Many pharmaceutically acceptable carriers are known in the art. It will be understood by those in the art that a pharmaceutically acceptable carrier must be compatible with the other ingredients of the formulation and tolerated by a subject in need thereof. Such compositions may be in the form of tablets, capsules, caplets, powders, granules, lozenges, suppositories, reconstitutable powders, or liquid preparations, such as oral or sterile parenteral solutions or suspensions.

The proportion of each carrier is determined by the solubility and chemical nature of the agent(s), the route of administration, and standard pharmaceutical practice. In order to ensure consistency of administration, in an embodiment of the present invention, the pharmaceutical composition is in the form of a unit dose. The unit dose presentation forms for oral administration may be tablets and capsules and may contain conventional excipients. Non-limiting examples of conventional excipients include binding agents such as acacia, gelatin, sorbitol, or polyvinylpyrolidone; fillers such as lactose, sugar, maize-starch, calcium phosphate, sorbitol or glycine; tabletting lubricants such as magnesium stearate; disintegrants such as starch, polyvinylpyrrolidone, sodium starch glycollate or microcrystalline cellulose; or pharmaceutically acceptable wetting agents such as sodium lauryl sulphate.

The compounds of the present invention may be injected parenterally; this being intramuscularly, intravenously, or subcutaneously. For parenteral administration, the compounds may be used in the form of sterile solutions containing solutes, for example sufficient saline or glucose to make the solution isotonic.

The compounds may be administered orally in the form of tablets, capsules, or granules, containing suitable excipients such as starch, lactose, white sugar and the like. The compounds of the invention may be administered orally in the form of solutions which may contain coloring and/or flavoring agents. The compounds of the invention may also be administered sublingually in the form of tracheas or lozenges in which the active ingredient(s) is/are mixed with sugar or corn syrups, flavoring agents and dyes, and then dehydrated sufficiently to make the mixture suitable for pressing into solid form.

The solid oral compositions may be prepared by conventional methods of blending, filling, tabletting, or the like. Repeated blending operations may be used to distribute the active agent(s) (i.e. inhibitors of aminoglycoside 6'-N-acetyltransferases) throughout those compositions employing large quantities of fillers. Such operations are, of course, conventional in the art. The tablets may be coated according to methods well known in normal pharmaceutical practice, in particular with an enteric coating.

Oral liquid preparations may be in the form of emulsions, syrups, or elixirs, or may be presented as a dry product for reconstitution with water or other suitable vehicles before use. Such liquid preparations may or may not contain conventional additives. Non limiting examples of conventional additives include suspending agents such as sorbitol, syrup, methyl cellulose, gelatin, hydroxyethylcellulose, carboxymethylcellulose, aluminum stearate gel, or hydrogenated edible fats; emulsifying agents such as sorbitan monooleate or acaci; non-aqueous vehicles (which may include edible oils), such as almond oil, fractionated coconut oil, oily esters selected from the group consisting of glycerine, propylene glycol, ethylene glycol, and ethyl alcohol; preservatives such as, for instance, methyl para-hydroxybenzoate, ethyl para-hydroxybenzoate, n-propyl parahydroxybenzoate, or n-butyl parahydroxybenzoate or sorbic acid; and, if desired, conventional flavoring or coloring agents.

For parenteral administration, fluid unit dosage forms may be prepared by utilizing the compounds and a sterile vehicle, and, depending on the concentration employed, the compounds may be either suspended or dissolved in the vehicle. Once in solution, the compounds may be injected and filter sterilized before filling a suitable vial or ampoule followed by subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying). Parenteral suspensions may be prepared in substantially the same manner, except that the inhibitor(s) of aminoglycoside 6'-N-acetyltransferases should be suspended in the vehicle rather than being dissolved, and, further, sterilization is not achievable by filtration. The inhibitor(s) of aminoglycoside 6'-N-acetyltransferases may be sterilized, however, by exposing it to ethylene oxide before suspending it in the sterile vehicle.

The pharmaceutical compositions of the present invention comprise a pharmaceutically effective amount of the compounds of the invention as described herein and one or more pharmaceutically acceptable carriers, excipients and/or diluents. In an embodiment of the present invention, the pharmaceutical compositions contain from about 0.1% to about 99% by weight of the compounds of the invention as disclosed herein. In a further embodiment of the present invention, the pharmaceutical compositions contain from about 10% to about 60% by weight of an inhibitor(s) of the compounds of the invention as disclosed herein, depending on which method of administration is employed. Physicians will determine the most-suitable dosage. Dosages may vary with the mode of administration and the particular compound of the invention. In addition, the dosage may vary with the particular patient under treatment. The dosage of a compound of the invention used in the treatment may vary, depending on the degree of bacterial resistance, the weight of the patient, the relative efficacy of the compound and the judgment of the treating physician.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "inhibition" is intended to mean a substantial slowing, interference, suppression, prevention, delay and/or arrest of a chemical or biochemical action.

The term "pharmacological inhibition" is intended to mean a substantial slowing, interference, suppression, prevention, delay and/or arrest of a chemical action which is caused by an effective amount of a compound, drug, or agent.

The term "inhibitor" is intended to mean a compound, drug, or agent that substantially slows, interferes, suppresses, prevents, delays and/or arrests a chemical action.

The terms "treatment" or "treating" are intended to mean obtaining a desired pharmacologic and/or physiologic effect, or an improvement in a disease condition in a subject or improvement of a symptom associated with a disease or a medical condition in a subject. The effect may be prophylactic in terms of completely or partially preventing a disease or symptom associated therewith and/or may be therapeutic in terms of a partial or complete cure for a disease and/or the pathophysiologic effect attributable to the disease. "Treatment" as used herein covers any treatment of a disease in a mammal and includes: (a) preventing a disease or condition from occurring in an individual who may be predisposed to the disease but has not yet been diagnosed as having it; (b) inhibiting the disease, (e.g., arresting its development); or (c) relieving the disease (e.g., reducing symptoms associated with the disease).

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include citric acid, lactic acid, tartaric acid, fatty acids, and the like. Pharmaceutically acceptable salts are known in the art. Other examples of suitable acids include but are not limited to hydrochloric, hydrobromic, perchloric, fumaric, maleic, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts. Salts derived from appropriate bases include alkali metal, alkaline earth metal or ammonium salts. The salt(s) must be "acceptable" in the sense of not being deleterious to the recipient thereof.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

The term "Solvate" means that a compound as defined herein incorporates one or more pharmaceutically acceptable solvents including water to give rise to hydrates. The solvate may contain one or more molecules of solvent per molecule of compound or may contain one or more molecules of compound per molecule of solvent. Illustrative non-limiting examples of hydrates include monohydrate, dihydrate, trihydrate and tetrahydrate or semi-hydrate. In one embodiment, the solvent may be held in the crystal in various ways and thus, the solvent molecule may occupy lattice positions in the crystal, or they may form bonds with salts of the compounds as described herein. The solvate(s) must be "acceptable" in the sense of not being deleterious to the recipient thereof. The solvation may be assessed by methods known in the art such as Loss on Drying techniques (LOD).

It will be appreciated by those skilled in the art that the compounds in accordance with the present invention can exist in several different crystalline forms due to a different arrangement of molecules in the crystal lattice. This may include solvate or hydrate (also known as pseudopolymorphs) and amorphous forms. All such crystalline forms and polymorphs are included within the scope of the invention. The polymorphs may be characterized by methods well known in the art. Examples of analytical procedures that may be used to determine whether polymorphism occurs include: melting point (including hot-stage microscopy), infrared (not in solution), X-ray powder diffraction, thermal analysis methods (e.g. differential scanning calorimetry (DSC) differential thermal analysis (DTA), thermogravimetric analysis (TGA)), Raman spectroscopy, comparative intrinsic dissolution rate, scanning electron microscopy (SEM).

As used herein, the term "pharmaceutically acceptable carrier" includes any and all solvents such as phosphate buffered saline, water, saline, dispersion media, coatings, antibacterial and antifungal agents, isotonic and absorption delaying agents and the like. The use of such media and agents for pharmaceutically active substances is well known in the art. Supplementary active ingredients can also be incorporated into the compositions. The pharmaceutical compositions of the invention can be formulated according to known methods for preparing pharmaceutically useful compositions. Formulations are described in a number of sources which are well known and readily available to those skilled in the art. For example, Remington's Pharmaceutical Science (Martin E W (1995) Easton Pa., Mack Publishing Company, 19th ed.) describes formulations which can be used in connection with the subject invention.

The present description refers to a number of chemical terms and abbreviations used by those skilled in the art. Nevertheless, definitions of selected terms are provided for clarity and consistency.

Abbreviations: AcCoA: Acetyl Coenzyme A; PanK: pantothenate kinase; PPAT:

phosphopantetheine adenylyltransferase; DPCK: dephosphocoenzyme A kinase; ACN: Acetonitrile; APCI: Atmospheric Pressure Chemical Ionization; CoA: Coenzyme A; COSY: $^1$H-$^1$H Correlation Spectroscopy; DCC: 1,3-Dicyclohexylcarbodimide; DCM: Dichloromethane; DCU: 1,3-Dicyclohexylcarbodiurea; DMAP: N,N-Dimethylaminopyridine; DTDP: 4,4'-Dithiodipyridine; DTT: 1,4-Dithiothreitol; DIPEA (Hunig's base): Diisopropyl ethyl amine: NBD:endo-N-Hydroxy-5-norbornene-2,3-dicarboximide; EDTA: Ethylenediaminetetraacetic acid; ESI: Electron Spray Ionization; EtOAc: Ethyl acetate; HEPES: 4-(2-hydroxyethyl)-1-piperazineethanesulfonic acid; Hex: Hexane; HMBC: $^1$H-$^{13}$C Heteronucleus Multiple Bond Correlation Spectroscopy; HRMS: High Resolution Mass Spectrometry; HSQC: $^1$H-$^{13}$C Heteronucleus Single Quantum Correlation Spectroscopy; LB: Luria-Bertani media; TEA: Triethylamine; THF: Tetrahydrofuran; TLC: Analytical Thin Layer Chromatography; TOCSY: Total Correlation Spectroscopy.

Preparation of the Compounds of the Invention

Some of the compounds of the present disclosure can be prepared according to the procedures denoted in the following reaction Scheme 1 and examples or modifications thereof using readily available starting materials, reagents, and conventional procedures or variations thereof well-known to a practitioner of ordinary skill in the art of synthetic organic chemistry. Specific definitions of variables in the Schemes are given for illustrative purposes only and are not intended to limit the procedures described.

Scheme 1: General synthesis of the compounds disclosed herein

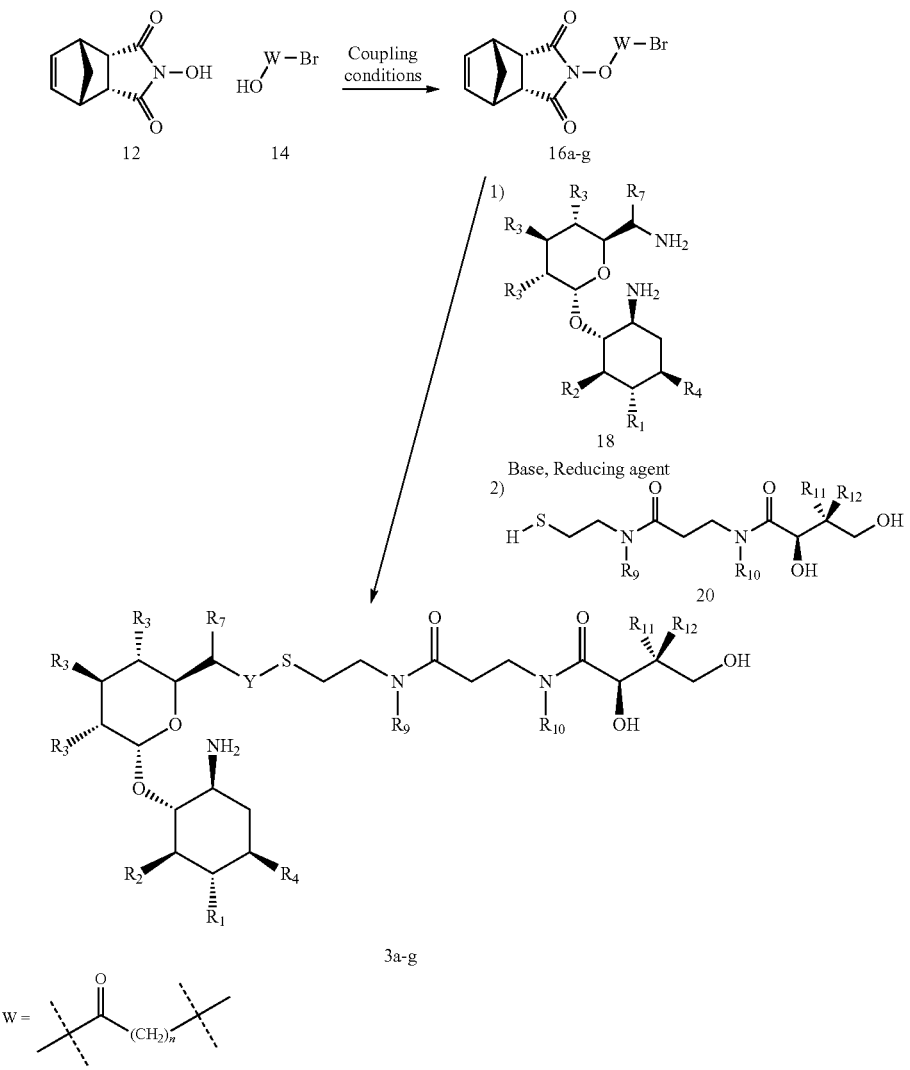

As illustrated in Scheme 1, endo-N-hydroxy-5-norbornene-2,3-dicarboximide (NBD) 12 is coupled with reagent 14 under typical conditions, for example using DCC in presence of DMAP in THF. Resulting intermediate 16a-g is then mixed with compound 18 in a protic solvent such as water. The resulting product is then added to a reaction mixture comprising reagent 20 mixed with a base such as DIPEA and with a reducing agent such as DTT. The desired product 3a-g is then obtained.

Compounds in which Y is

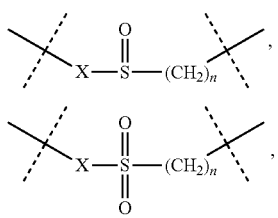

and X is O, can be obtained by the methods described in Gao, Feng et al. Bioorg. Med. Chem. Let. 18 (2008) 5518-5522.

General methods. All reagents were purchased from Sigma-Aldrich Canada Ltd. Reagents and solvents were used without further purification unless otherwise stated. Flash chromatography and TLC analysis (F-254) were performed with 60 Å silica gel from Silicycle (Quebec, Canada).

HPLC purification. Compounds 3a-g were purified by reversed-phase HPLC using an Agilent 1100 modular system equipped with an autosampler, a quaternary pump system, a photodiode array detector, a thermostatted column compartment, and a ChemStation (for LC 3D A.09.03) data system. The columns used for purification/purity tests are a semi-preparative 10×250 mm, Luna 5μ CN 100A (Phenomenex, CA), a semi-preparative 9.4×250 mm, Zorbax 300 SB-C8 (Agilent, CA), and a preparative 21.20×250 mm, Luna 5μ CN 100A (Phenomenex, CA). Samples were eluted at a flow rate of 2 mL min$^{-1}$ for the semi-preparative columns and 3 mL min$^{-1}$ for the preparative column, using a combination of mobile phase A (0.05% aqueous TFA) and mobile phase B (acetonitrile containing 0.05% TFA). The detector was set to 214 nm. Two of methods 1-4 were employed for purification as indicated in Table 1. For determination of purity, method 5 was employed.

Instrumentation. High resolution mass spectra were acquired on an EXACTIVE instrument in orbitrap mode. Low resolution mass spectra were obtained using a Finnigan LCQDUO mass spectrometer with ESI without fragmentation. $^1$H and $^{13}$C NMR spectra were recorded using Varian mercury 300 and 500 spectrometer. The chemical shifts (δ) are reported in parts per million (ppm) and are referenced to either the internal standard RMS (when CDCl$_3$ is used) or the deuterated solvent used. The peak patterns are indicated as follows: s, singlet; d, doublet; t, triplet; dt, doublet of triplet; ddd, doublet of doublet of doublet; td, triplet of doublet; m, multiplet; q, quartet; p, pentet; and br s, broad singlet. The coupling constants, J, are reported in hertz (Hz).

TABLE 1

Linear gradient profiles for HPLC purification and purity analysis.

| Time (min) | % A (0.05% TFA in H$_2$O) | % B (0.05% TFA in ACN) |
|---|---|---|
| Method 1 (with semi-preparative Luna 5μ CN column) | | |
| 0 | 99 | 1 |
| 3 | 99 | 1 |
| 23 | 80 | 20 |
| 30 | 60 | 40 |
| 37 | 1 | 99 |
| 40 | 1 | 99 |
| 47 | 99 | 1 |
| 50 | 99 | 1 |
| Method 2 (with semi-preparative Zorbax 300 SB-C8 column) | | |
| 0 | 99 | 1 |
| 20 | 90 | 10 |
| 25 | 99 | 1 |
| 30 | 99 | 1 |
| Method 3 (with preparative Luna 5μ CN column) | | |
| 0 | 99 | 1 |
| 5 | 99 | 1 |
| 25 | 60 | 40 |
| 37 | 1 | 99 |
| 42 | 1 | 99 |
| 55 | 99 | 1 |
| 60 | 99 | 1 |
| Method 4 (with semi-preparative Luna 5μ CN column) | | |
| 0 | 99 | 1 |
| 20 | 90 | 10 |
| 25 | 99 | 1 |
| 30 | 99 | 1 |
| Method 5 (with semi-preparative Zorbax 300 SB-C8 column) | | |
| 0 | 99 | 1 |
| 10 | 1 | 99 |
| 12 | 1 | 99 |
| 22 | 99 | 1 |
| 25 | 99 | 1 |

General Procedure for synthesis of compounds 16 from reagent 14. endo-N-Hydroxy-5-nornornene-2,3-dicarboximide (NBD) (1.07 g, 6 mmol) and the corresponding carboxylic acid (6 mmol, 14) were dissolved in dichloromethane (50 mL). DCC (1.24 g, 6 mmol) was added to the mixture, followed by a catalytic amount of DMAP (~20 mg). A few minutes after addition of DCC, a white solid (DCU) precipitated out. The reaction was stirred at room temperature overnight. The presence of the desired NBD ester (16) was monitored by TLC (1:1 ethyl acetate:hexanes, $R_f$=0.45-0.50). The solid DCU was removed by filtration and the filtrate was evaporated to approximately 1 mL. Flash column chromatography (ethyl acetate:hexanes 1:2) was used to purify the desired compounds, which typically appeared as white, flakey solids upon evaporation of all solvents (yields 64-82%).

General Procedure for synthesis of compound 3a-g. The free base of neamine, ribostamycin or kanamycin (0.45 mmol, 145 mg for neamine) was dissolved in water (3 mL), and the corresponding NBD ester (16, 0.23 mmol) was dissolved in acetone (2 mL). The two solutions were mixed and stirred for between 10 min and 20 min depending on the intermediate 16. In another vial, D-pantethine 20 (66 mg, 0.12 mmol), DIPEA (1 mL, 5.7 mmol), and DTT (20 mg, 0.13 mmol) were mixed in acetone (2 mL) and sonicated until a homogenous mixture is obtained. This solution was then transferred to the respective aminoglycoside/NBD ester reaction mixture and then allowed to stir overnight. The solvent was evaporated under vacuum and the residue redissolved in water (10 mL). TFA was added to pH ~3, which was then followed by three successive ethyl acetate washes. The aqueous layer was evaporated to dryness by lyophilization. HPLC purification was achieved through method 3 followed by method 4. Compounds all appear as white fluffy powders after lyophilization (yields 20-50%).

Procedure for synthesis compounds 2e. Neamine free base (52 mg, 0.16 mmol) was dissolved in water (2 mL) whereas the NBD ester 16 (16 mg, 0.08 mmol) was dissolved in acetone (2 mL). The two solutions were mixed and stirred for 20 min. In another vial, CoA (30 mg, 0.04 mmol), was dissolved in triethylammonium-bicarbonate buffer (2 mL, 1 M, pH 8.4-8.6) and sonicated until a homogenous mixture was obtained. This solution was then transferred to the neamine/16 reaction mixture and allowed to stir overnight. The solvent was evaporated under vacuum and the residue dissolved in water (10 mL). TFA was added to pH ~3, which was then followed by three successive ethyl acetate washes. Water was evaporated by lyophilization. HPLC purification was achieved first through method 1, followed by method 2. Compound was a white fluffy powder after lyophilization (6.9 mg, 15%).

N-hydroxy-5-norbornene-2,3-dicarboximide bromoacetate (16a). Yield: 1.4 g, 64%. $^1$H NMR (CDCl$_3$, 300 MHz): δ 6.19 (br s, 2H), 4.03 (s, 2H), 3.44 (br s, 2H), 3.33 (br s, 2H), 1.77 (d, J=9.0, 1H), 1.52 (d, J=9.0, 1H). $^{13}$C NMR (CDCl$_3$, 75 MHz): δ 169.5, 134.8, 51.2, 44.7, 43.3, 21.5

N-hydroxy-5-norbornene-2,3-dicarboximide bromopropanoate (16b). Yield: 1.4 g, 68%. $^1$H NMR (CDCl$_3$, 300 MHz): δ 6.19 (br s, 2H), 3.57 (t, J=6.9, 2H), 3.44 (br s, 2H), 3.33 (br s, 2H), 3.15 (t, J=6.9, 2H), 1.79 (d, J=9.0, 1H), 1.53 (d, J=9.0, 1H). $^{13}$C NMR (CDCl$_3$, 75 MHz): δ 169.6, 134.7, 51.2, 44.7, 43.2, 34.6, 23.5.

N-hydroxy-5-norbornene-2,3-dicarboximide bromobutanoate (16c). Yield: 1.5 g, 76%. $^1$H NMR (CDCl$_3$, 300 MHz): δ 6.19 (br s, 2H), 3.48 (t, J=6.0, 2H), 3.44 (br s, 2H), 3.33 (br s, 2H), 2.75 (t, J=6.0, 2H), 2.25 (p, J=6, 2H), 1.79 (d, J=9.0, 1H), 1.53 (d, J=9.0, 1H). $^{13}$C NMR (CDCl$_3$, 75 MHz): δ 169.9, 134.7, 51.3, 44.7, 43.3, 31.6, 29.4, 27.4

N-hydroxy-5-norbornene-2,3-dicarboximide bromopentanoate (16d). Yield: 1.5 g, 80%. $^1$H NMR (CDCl$_3$, 300 MHz): δ 6.18 (br s, 2H), 3.43-3.39 (m, 4H), 3.31 (br s, 2H), 2.58 (t, J=6.9, 2H), 2.00-1.83 (m, 4H), 1.77 (d, J=9.0, 1H), 1.52 (d, J=9.0, 1H). $^{13}$C NMR (CDCl$_3$, 75 MHz): δ 699, 134.7, 51.3, 44.7, 43.3, 32.7, 31.3, 29.9, 23.1

N-hydroxy-5-norbornene-2,3-dicarboximide bromohexanoate (16e). Yield: 1.5 g, 82%. $^1$H NMR (CDCl$_3$, 300 MHz) δ 6.18 (br s, 2H), 3.43 (br s, 2H), 3.39 (t, J=6.6, 2H), 3.31 (br s, 2H). 2.55 (t, J=7.2, 2H), 1.92-1.49 (m, 8H). $^{13}$C NMR (CDCl$_3$, 75 MHz): δ 170.0, 134.7, 51.3, 44.7, 43.3, 33.2, 32.2, 30.7, 27.3, 23.7. HRMS for C$_{15}$H$_{18}$BrNO$_4$ [M+Na]+ calcd. 378.0317. found 378.0326.

Neamine 6'-N—(R)-(3-((2-((2-amino-2-oxoethyl)thio)ethyl)amino)-3-oxopropyl)-2,4-dihydroxyl-3,3-dimethylbutanamide (3a). Yield: 66 mg, 45%. Purity>99%. Method 3, t$_R$=25.68 min, Method 4, t$_R$=8.20 min. $^1$H NMR (D$_2$O, 300 MHz) δ 5.57 (d, J=3.9, 1H), 3.81 (s, 1H), 3.78-3.67 (m, 3H), 3.53-3.12 (m, 19H), 2.56 (t, J=6.6, 2H), 2.39-2.31 (m, 3H), 1.72 (m, 1H), 0.74 (s, 3H), 0.71 (s, 3H). $^{13}$C NMR (D$_2$O, 300 MHz) δ 174.9, 173.8, 173.1, 96.6, 78.7, 75.6, 74.9, 72.4, 71.4, 70.3, 68.6, 68.2, 53.7, 49.6, 48.4, 39.4, 38.5, 38.1, 35.3, 35.2, 34.6, 31.2, 28.2, 20.4, 19.0. HRMS for C$_{25}$H$_{48}$N$_6$O$_{11}$S [M+H]+ calcd. 641.3175. found 641.3156.

Neamine 6'-N—(R)-(3-((2-((2-amino-2-oxopropyl)thio)ethyl)amino)-3-oxopropyl)-2,4-dihydroxyl-3,3-dimethylbutanamide (3b). Yield: 50 mg, 33%. Purity>98%. Method 3, t$_R$=23.43 min, Method 4, t$_R$=8.14 min. $^1$H NMR (D$_2$O, 300 MHz) δ 5.56 (d, J=3.9, 1H), 3.81 (s, 1H), 3.78-3.66 (m, 3H), 3.54-3.12 (m, 17H), 2.67 (t, J=6.9z, 2H), 2.52 (t, J=6.6, 2H), 2.42 (t, J=6.6, 2H), 2.31-2.37 (m, 3H), 1.71 (m, 1H), 0.74 (s, 3H), 0.71 (s, 3H). $^{13}$C NMR (D$_2$O, 300 MHz) δ 175.0, 174.9, 173.8, 96.7, 78.7, 75.6, 74.9, 72.4, 71.5, 70.1, 68.5, 68.2, 53.7, 49.6, 48.4, 39.0, 38.5, 38.5, 35.4, 35.3, 35.2, 30.2, 28.1, 26.8, 20.4, 19.0, HRMS for C$_{26}$H$_{50}$N$_6$O$_{11}$S [M+H]+ calcd. 655.3331. found 655.3310.

Neamine 6'-N—(R)-(3-((2-((2-amino-2-oxobutyl)thio)ethyl)amino)-3-oxopropyl)-2,4-dihydroxyl-3,3-dimethylbutanamide (3c). Yield: 30 mg, 20%. Purity>99%. Method 3, t$_R$=29.55 min, Method 4, t$_R$=8.40 min. $^1$H NMR (D$_2$O, 300 MHz) δ 5.55 (d, J=3.6, 1H), 3.81 (s, 1H), 3.78-3.66 (m, 3H), 3.52-3.05 (m, 17H), 2.52 (t, J=6.6, 2H), 2.41 (t, J=6.9, 2H), 2.37-2.31 (m, 3H), 2.23 (t, J=7.2, 2H), 1.77-1.64 (m, 3H), 0.74 (s, 3H), 0.71 (s, 3H). $^{13}$C NMR (D$_2$O, 300 MHz) δ 176.5, 174.9, 173.8, 96.7, 78.8, 75.6, 74.9, 72.4, 71.5, 70.1, 68.5, 68.2, 53.7, 49.5, 48.4, 38.9, 38.5, 38.5, 35.3, 35.2, 34.4, 30.1, 30.0, 28.1, 24.9, 20.4, 19.0. HRMS for C$_{27}$H$_{52}$N$_6$O$_{11}$S [M+H]+ calcd. 669.3499. found 669.3472.

Neamine 6'-N—(R)-(3-((2-((2-amino-2-oxopentyl)thio)ethyl)amino)-3-oxopropyl)-2,4-dihydroxyl-3,3-dimethylbutanamide (3d). Yield: 60 mg, 38%. Purity>93%. Method 3, t$_R$=33.68 min, Method 4, t$_R$=9.06 min. $^1$H NMR (D$_2$O, 300 MHz) δ 5.55 (d, J=3.9, 1H), 3.81 (s, 1H), 3.78-3.66 (m, 3H), 3.54-3.06 (m, 17H), 2.52 (t, J=6.6, 2H), 2.43 (t, J=7.2, 2H), 2.38-2.31 (m, 3H), 2.15 (t, J=7.2, 2H), 1.71 (m, 1H), 1.57-1.37 (m, 4H), 0.75 (s, 3H), 0.72 (s, 3H). $^{13}$C NMR (D$_2$O, 300 MHz) δ 177.2, 174.9, 173.8, 96.6, 78.8, 75.6, 74.9, 72.4, 71.5, 70.0, 68.5, 68.2, 53.7, 49.5, 48.4, 38.6, 38.5, 38.5, 35.3, 35.2, 35.1, 30.3, 30.2, 28.2, 28.0, 24.4, 20.4, 19.0. HRMS for C$_{28}$H$_{54}$N$_6$O$_{11}$S [M+H]+ calcd. 683.3571. found 683.3665.

Neamine 6'-N—(R)-(3-((2-((2-amino-2-oxohexyl)thio)ethyl)amino)-3-oxopropyl)-2,4-dihydroxyl-3,3-dimethylbutanamide (3e). Yield: 80 mg, 50%. Purity>98%. Method 3, t$_R$=34.28 min, Method 4, t$_R$=9.30 min. $^1$H NMR (D$_2$O, 300 MHz) δ 5.55 (d, J=3.6, 1H), 3.81 (s, 1H), 3.77-3.65 (m, 3H), 3.52-3.11 (m, 17H), 2.51 (t, J=6.6, 2H), 2.41 (t, J=6.9, 2H), 2.37-2.30 (m, 3H), 2.12 (t, J=7.2, 2H), 1.70 (m, 1H), 1.49-1.38 (m, 4H), 1.26-1.18 (m, 2H), 0.74 (s, 3H), 0.71 (s, 3H). $^{13}$C NMR (D$_2$O, 75 MHz) δ 177.6, 174.9, 173.7, 96.7, 78.8, 75.6, 74.9, 72.4, 71.5, 70.1, 68.5, 68.2, 53.7, 49.5, 48.4, 38.8, 38.5, 38.5, 35.5, 35.4, 35.2, 30.6, 30.1, 28.2, 28.1, 27.3, 24.8, 20.4, 18.9. HRMS for C$_{29}$H$_{56}$N$_6$O$_{11}$S [M+Na]+ calcd. 719.3728. found 719.3640.

Ribostamycin 6'-N—(R)-(3-((2-((2-amino-2-oxohexyl)thio)ethyl)amino)-3-oxopropyl)-2,4-dihydroxyl-3,3-dimethylbutanamide (3f). Yield: 18 mg, 20%. $^1$H NMR (D$_2$O, 300 MHz) δ 5.71 (d, J=4.2, 1H), 5.19 (s, 1H), 3.52-3.11 (m, 27H), 2.52 (t, J=6.6, 2H), 2.42 (t, J=7.2, 2H), 2.35-2.31 (m, 3H), 2.13 (t, J=7.2, 2H), 1.76-1.61 (m, 1H), 1.49-1.38 (m, 4H), 1.27-1.17 (m, 2H), 0.75 (s, 3H), 0.71 (s, 3H). $^{13}$C NMR (D$_2$O, 75 MHz) δ 177.6, 174.9, 173.7, 110.0, 95.7, 84.5, 82.4, 75.7, 75.6, 75.2, 72.4, 71.5, 69.9, 68.9, 68.4, 68.2, 60.6, 53.6, 49.6, 48.4, 38.7, 38.5, 38.4, 35.4, 35.3, 35.2, 30.7, 30.2, 28.2, 27.6, 27.2, 24.8, 20.4, 18.9.

Kanamycin 6'-N—(R)-(3-((2-((2-amino-2-oxohexyl)thio)ethyl)amino)-3-oxopropyl)-2,4-dihydroxyl-3,3-dimethylbutanamide (3 g). Yield: 47 mg, 24%. $^1$H NMR (D$_2$O, 300 MHz) δ 5.28 (d, J=3.9, 1H), 4.93 (d, J=3.6, 1H), 3.81-3.11 (m, 29H), 2.51 (t, J=6.6, 2H), 2.41 (t, J=7.2, 2H), 2.35-2.30 (m, 3H), 2.11 (t, J=7.2, 2H), 1.80-1.68 (m, 1H), 1.49-1.38 (m, 4H), 1.26-1.16 (m, 2H), 0.74 (s, 3H), 0.70 (s, 3H). $^{13}$C NMR (D$_2$O, 75 MHz) δ 177.5, 174.9, 173.7, 100.4, 97.9, 83.5, 81.72, 79.2, 75.6, 72.9, 72.7, 72.6, 72.0, 71.1, 71.0, 69.9, 68.2, 68.0, 65.2, 59.6, 54.9, 49.6, 48.1, 38.5, 38.4, 35.5, 35.4, 35.2, 30.7, 30.2, 28.2, 27.6, 27.2, 24.8, 20.4, 18.9.

Neamine-CoA bisubstrate 2e. Yield: 6.9 mg, 15%. Purity>99%. Method 1, t$_R$=14.56 min, Method 2, t$_R$=26.17 min. $^1$H NMR (D$_2$O, 500 MHz) δ 8.54 (s, 1H), 8.34 (s, 1H), 6.11 (d, J=5.0, 1H), 5.61 (d, J=3.5, 1H), 4.47 (br s, 1H), 4.20-4.09 (m, 2H), 3.89 (s, 1H), 3.85-3.71 (m, 4H), 3.53-3.18 (m, 13H), 2.51 (t, J=6.5, 2H), 2.43-2.39 (m, 3H), 2.35 (t, J=6.5, 2H), 2.15 (t, J=6.5, 2H), 1.83 (m, 1H), 1.48-1.39 (m, 4H), 1.25-1.18 (m, 2H), 0.81 (s, 3H), 0.69 (s, 3H). $^{13}$C NMR (D$_2$O, 125 MHz) δ 177.5, 174.5, 173.8, 149.5, 148.4, 144.7, 142.3, 118.5, 96.7, 87.5, 83.2, 79.1, 74.9, 74.2, 73.8, 72.4, 72.2, 71.9, 71.6, 70.2, 68.6, 65.0, 53.8, 49.7, 48.5, 39.1, 38.7, 38.3, 38.2, 35.4, 35.3, 35.2, 30.8, 30.2, 28.2, 27.2, 24.8, 20.8, 18.3. LRMS for C$_{39}$H$_{70}$N$_{11}$O$_{23}$P$_3$S [M+H]+ calcd. 1186.36. found 1186.21.

The aminoglycoside 6'-N-acetyltransferases AAC(6')-li and AAC(6')-ly are important enzymes involved in causing resistance to aminoglycoside antibiotics. For the purposes of the present invention, AAC(6')-li and AAC(6')ly were selected because they are chromosomally encoded in *Enterococcus faecium* and *Salmonella enterica* respectively, which are leading causes of hospital-acquired infections. However, it is to be understood that any of the other known aminoglycoside 6'-N-acetyltransferases [AAC(6')s] are also included for the purposes of the present invention.

AAC(6')-li is a member of the GCN5-related N-acetyltransferase (GNAT) superfamily [Wybenga-Groot, L. E.; Draker, K.-A.; Wright, G. D.; Berghuis, A. M. Structure 1999, 7, 497-507]. These enzymes have a highly conserved structure around the acetyl CoA binding pocket, whereas residues around the second binding site have poorly conserved sequences, explaining the diversity of substrates ranging from histones to aminoglycoside antibiotics [Marmorstein, R. J. Mol. Biol. 2001, 311, 433-444].

The compounds described herein are devoid of inhibitory activity against purified AAC(6')-li up to 500 μM. To investigate that the compounds 3a-e can be phosphorylated through the CoA biosynthetic pathway, kinetic studies were performed using purified PanK, which is the rate-limiting enzyme of this pathway. The calculated Michaelis-Menten constants (K$_m$) and turnover rates (k$_{cat}$) are shown in Table 2 for the PanK mediated transformation of 3a-e. The observed trend shows a correlation between the linker length and catalytic efficiency. Derivatives with longer linkers (i.e. compounds 3b-e, n=2 to 5) are generally better PanK substrates, whereas those with shorter linkers (i.e. compound 3a, n=1)

are poorer substrates. Although none approach the Km of the natural substrate pantothenic acid, 3d and 3e are comparable to the substrate pantetheine.

TABLE 2

Michaelis-Menten constants ($K_m$), turnover rates ($k_{cat}$) and catalytic efficiencies ($K_m/k_{cat}$) calculated for the transformation of compounds 3a-e by PanK (Pantothenate Kinase).

| Compound | $K_m$ (µM) | $k_{cat}$ (sec$^{-1}$) | $k_{cat}/K_m$ (µM$^{-1}$ sec$^{-1}$) |
|---|---|---|---|
| Pantothenic acid | 17 ± 2[a] | 1.07 ± 0.04[a] | 0.064 ± 0.008 |
| Pantetheine | 91 ± 10[b] | 0.32 ± 0.02[b] | 0.0035 ± 0.0004 |
| 3a | ≥500 | | |
| 3b | 480 ± 160 | 0.47 ± 0.05 | 0.0010 ± 0.0003 |
| 3c | 350 ± 80 | 0.50 ± 0.05 | 0.0014 ± 0.0004 |
| 3d | 230 ± 69 | 0.52 ± 0.08 | 0.0023 ± 0.0008 |
| 3e | 170 ± 50 | 0.66 ± 0.08 | 0.39 .0012 |

[a]Strauss E, Begley TP J Biol Chem. 2002, 277: 48205-48209;
[b]Worthington AS, Bukart MD, 2006Org Biomol Chem 4: 44-46.

Figure 3:
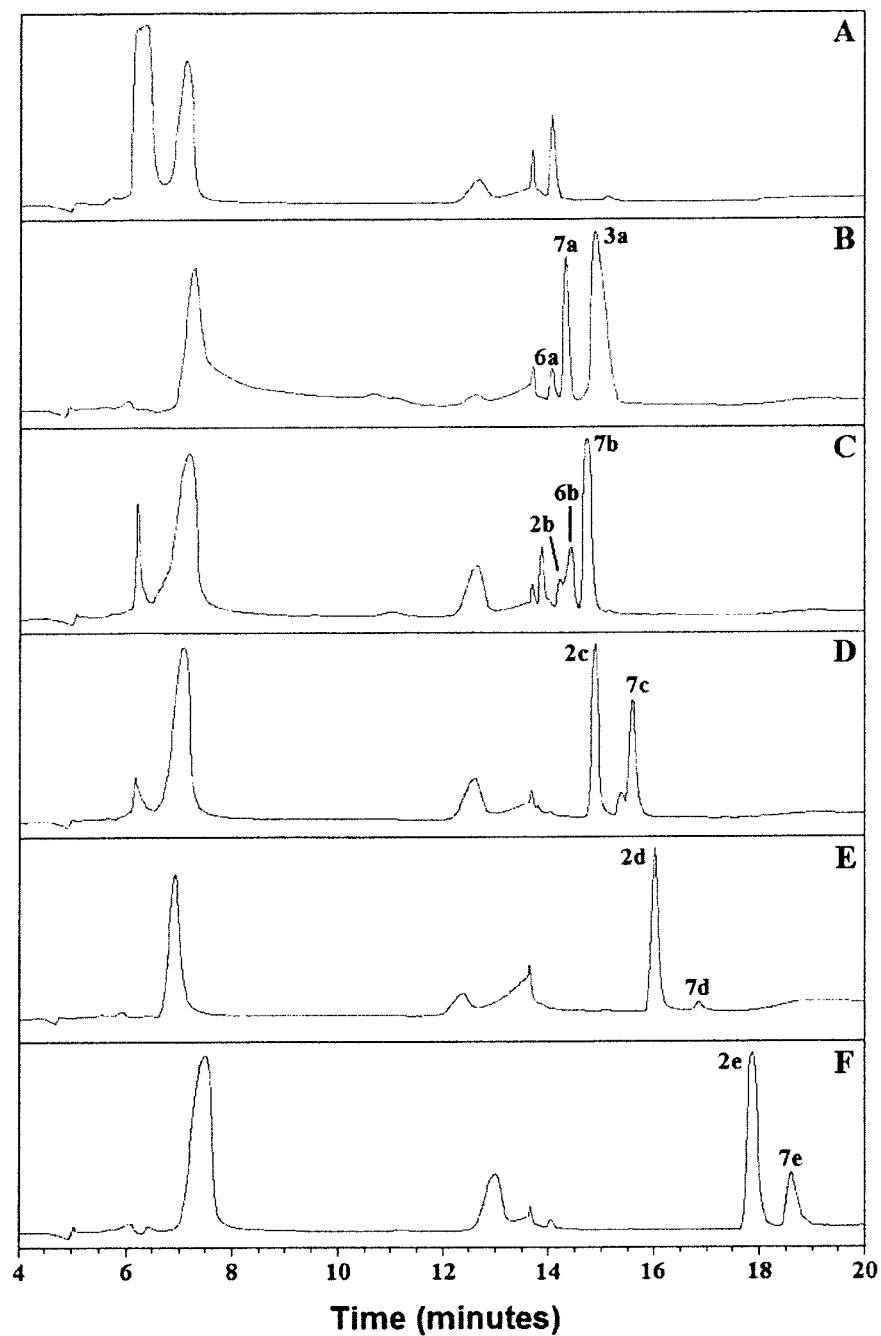
FIG. 3 shows HPLC traces illustrating the comparative biotransformations of compounds 3a-e by a combination of PanK, PPAT and DPCK. Reaction mixtures were incubated with (A) water, (B) 3a, (C) 3b, (D) 3c, (E) 3d, and (F) 3e.
Figure 4:
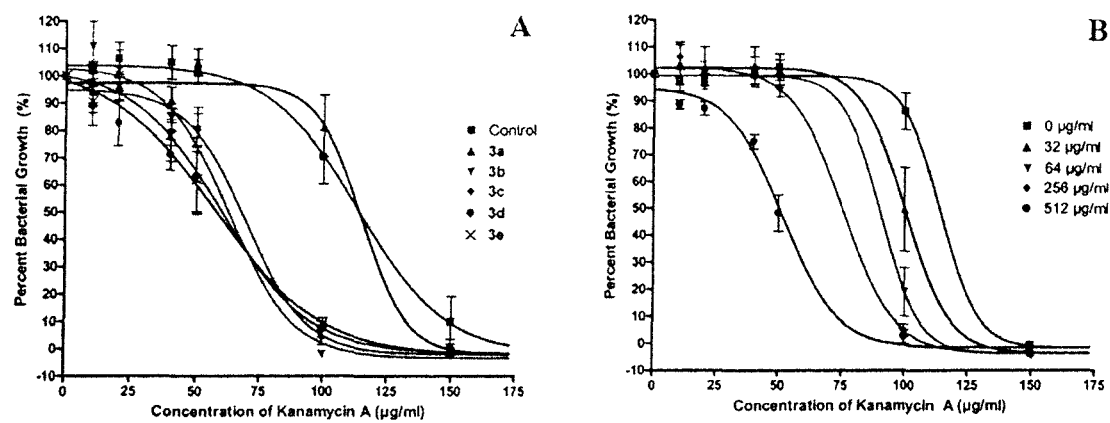
FIG. 4 shows the potentiation of kanamycin A activity against a resistant strain of E. faecium by compounds 3a-e (512 µg/ml) (panel A) and the dose dependent potentiation of kanamycin A activity against a resistant strain of E. faecium mediated by compound 3c (panel B).

A biosynthetic in vitro assay was designed to determine the propensity of compounds 3a-e to be fully extended to compounds 2a-e by the enzymes PanK, PPAT, and DPCK. With reference to FIG. 3, LC/MS analysis of the reaction mixture shows the transformation of 3e to 2e. With reference to FIG. 4, a product with a mass corresponding to each of 2a-e is clearly observed for all but the reaction of 3a (panel B FIG. 4). Moreover, the biosynthetic intermediates 6a-c and 7a-e are also identifiable as intermediates. Production of intermediates 6a and 6b (panel B FIG. 4) demonstrates that while PanK is able to transform 3a, it does so much less effectively. Our inability to calculate kinetic constants for this transformation (Table 2) is explained by a poor catalytic efficiency. The absence of detectable amounts of 6d and 6e (panels E and F FIG. 3) is attributed to a rapid transformation of 3d and 3e, to 2d and 2e respectively. Table 3 summarizes the approximate conversions of 3a-e to 2a-e, 6a-e and 7a-e. The data is consistent with an increased efficiency of PanK, PPAT and DPCK as a function of chain length. Although the data collected for 3d and 3e suggest a more complete transformation of 3d compared to 3e, the difference is within error. Overall, these results suggest that 3b-e may be extended by bacteria to the full bisubstrates 2b-e, which may in turn inhibit AAC(6').

TABLE 3

Approximate ratio of starting material and the different products (expressed as a relative percentage ± 5%) measured by HPLC for the in vitro transformation of 3a-e by a combination of PanK, PPAT and DPCK. Data points are the average of duplicate experiments.

| | Compounds detected by LC-MS | | | |
|---|---|---|---|---|
| Substrate | 3a-e | 6a-e | 7a-e | 2a-e |
| 3a | 70% | 5% | 25% | |
| 3b | | 20% | 70% | 10% |
| 3c | | 5% | 40% | 55% |
| 3d | | | 10% | 90% |
| 3e | | | 20% | 80% |

These in vitro results encouraged us to test 3a-e in cells. *Enterococcus faecium* is one of the leading causes of hospital-acquired infections. As mentioned above, the AAC(6')-li isoform is chromosomally encoded in *E. faecium*, thus conferring aminoglycoside resistance to this microorganism. The ability of 3a-e to resensitize *E. faecium* ATCC 19434 to the clinically used aminoglycoside kanamycin A was investigated using a standard checkerboard assay. The unaffected bacterial growth after treatment of this strain with 3a-e in the absence of kanamycin A demonstrates the lack of intrinsic antibacterial activity of compounds tested (FIG. 4A, 100% growth at 0 µg/mL kanamycin A). This is also the case when 3a-e are tested for antibacterial activity against *Staphylococcus aureus* ATCC 29213 and 43300, *Acinetobacter baumannii* ATCC 19606, *Pseudomonas aeruginosa* ATCC 27853, *Klebsiella penumoniae* ATCC 13883, and *Escherichia coli* ATCC 25922 and 11775.

In the absence of compounds 3a-e, the minimum concentration of kanamycin A causing a 50% growth inhibition ($MIC_{50}$) of *E. faecium* is in the order of 125 µg/mL (control trace in FIG. 4A). As expected from the in vitro data, addition of 3a had a negligible effect on the $MIC_K$ of kanamycin A. Compounds 3b-3e on the other hand decrease the $MIC_{50}$ of kanamycin A significantly, with 3d and 3e having the most significant effect in causing the $MIC_K$ to drop by half compared to that of kanamycin A alone. It is noteworthy that for each of the compounds 3b-e, a dose-dependent effect is observed, as exemplified with compound 3c illustrated in FIG. 4B.

Figure 5A:
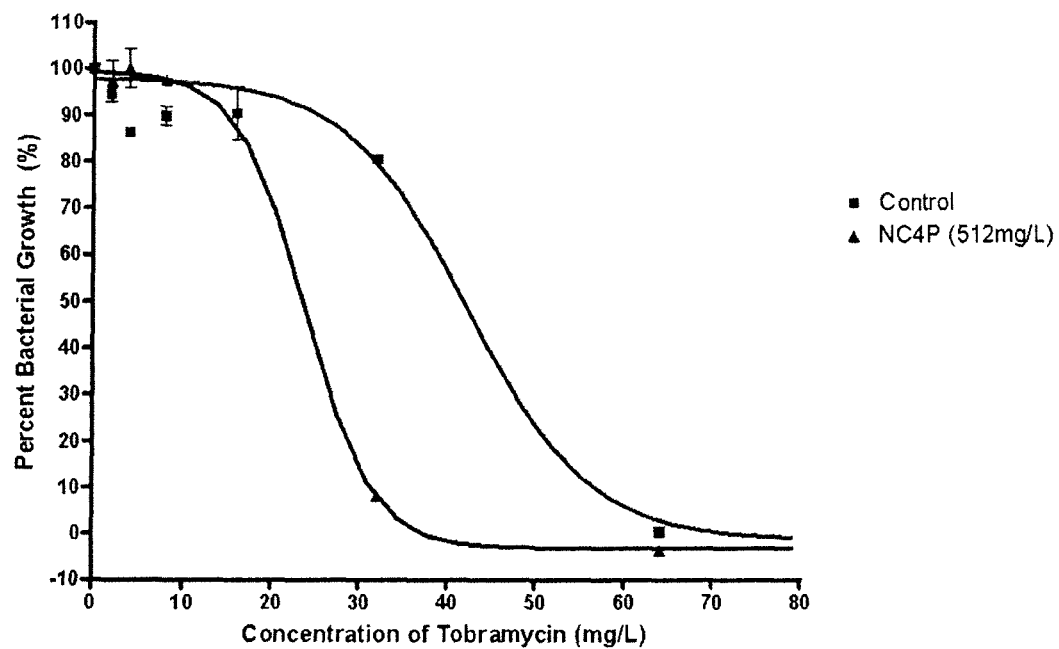
FIGS. 5A and 5B shows the potentiation of tobramycin activity against a resistant strain of E. faecium by compounds 3d (corresponding to NC4P in FIGS. 5A and B) 3e (corresponding to NC5P in FIG. 5B) and 3f (corresponding to RC5P in FIG. 5B) (512 µg/ml).
Figure 5B:
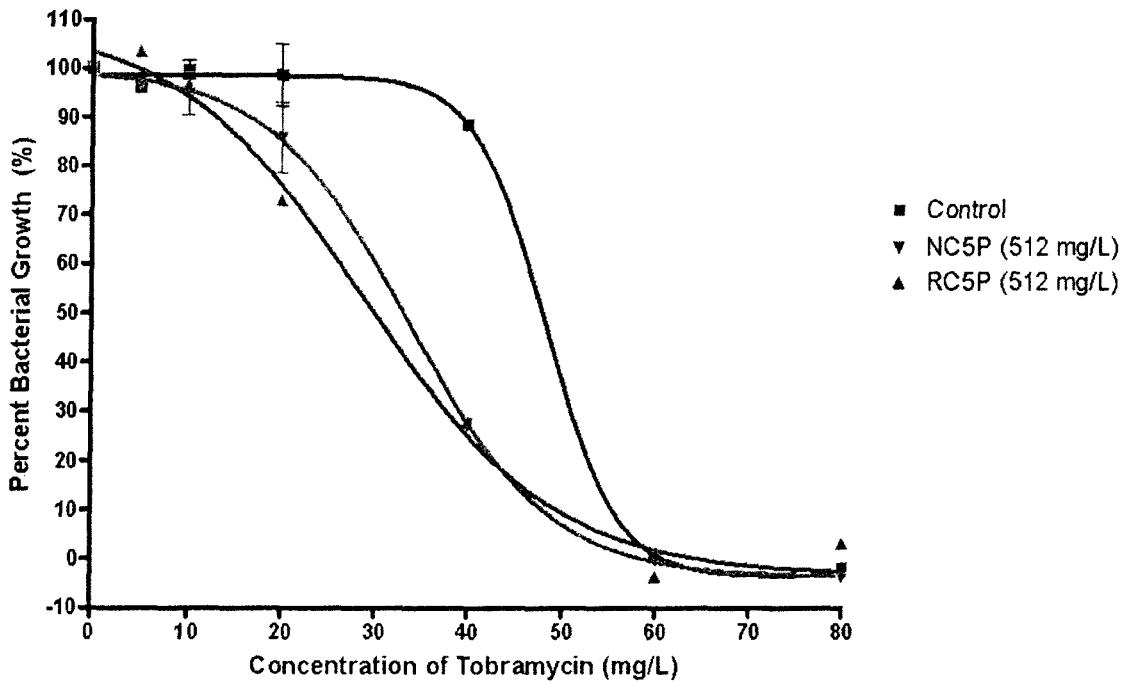
Figure 6:
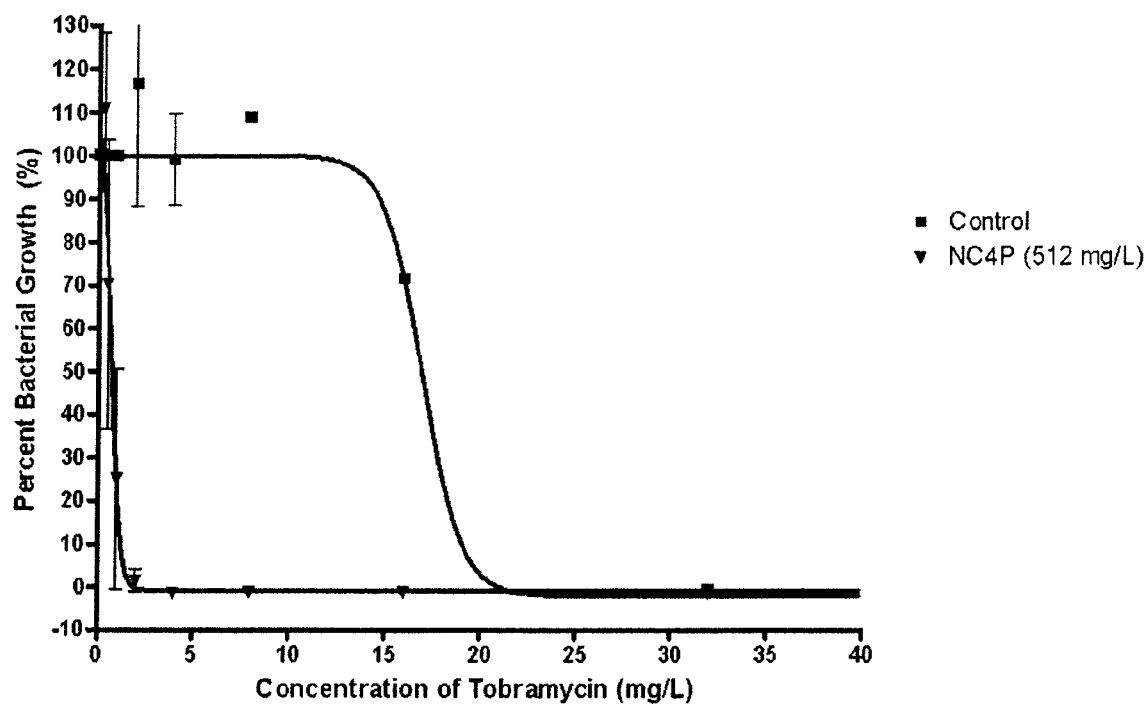
FIG. 6 shows the potentiation of tobramycin activity against a resistant strain of E. coli (BL21) harbouring AAC (6')-li resistance gene in pET-22b(+) vector by compound 3d (corresponding to NC4P).

The ability of compounds 3d (corresponding to NC4P in FIG. 5A), 3e (corresponding to NC5P in FIG. 5B) and 3f (corresponding to RC5P in FIG. 5B) to resensitize *E. faecium* ATCC 19434 and compound 3d (corresponding to NC4P in FIG. 6) to resensitize *E. coli* (BL21) to the clinically used aminoglycoside tobramycin was also investigated using the same assay as for kanamycin A described above. As expected, compounds 3d, 3e and 3f decrease the $MIC_{50}$ of tobramycin against *E. faecium* by about half, compared to that of tobramycin alone. This is comparable to the potion obtained for kanamycin. Moreover, data with an *E. coli* strain engineered to express the same AAC(6') isoform, show a 10-fold reduction in the MIC of tobramycin against this resistance strain when the aminoglycoside is combined with 3d General biological methods. *Enterococcus faecium* ATCC 19434, *Staphylococcus aureus* ATCC 29213 and 43300, *Acinetobacter baumannii* ATCC 19606, *Pseudomonas aeruginosa* ATCC 27853, *Klebsiella penumoniae* ATCC 13883, and *Escherichia coli* ATCC 25922 and 11775 were all purchased from Cedarlane (Burlington, ON). *E. faecium* was grown in Difco brain heart infusion media (BD, Mississauga, ON), *S. aureus* and *P. aeruginosa* were grown in Trypticase soy media (BD, Mississauga, ON), and *E. coli, A. baumannii*, and *K. pneumoniae* were grown in Nutrient media (BD, Mississauga, ON). Antibacterial tests were performed using Falcon™ Black with Clear Bottom 96-well Microtest™ Optilux plates (BD, Mississauga, ON).

AAC(6')-li inhibition assay. The AAC(6')-li inhibition assay was conducted with a BioLogic (Knoxville, Tenn.) SFM 400 stopped-flow mixing chamber controlled by an MPS-60 unit. The data was collected on a MOS 250 UV/Vis spectrophotometer at 412 nm. The TC-100 cuvette used had an observation path length of 1 cm. Data was processed with Biokine32 ver 4.2 (BioLogic) to determine initial rates, which were next fitted in Prism 4.0 (GraphPad) to determine kinetic parameters. The total reaction volume was 440 µL, from 4 reagent-containing chambers each containing an equal volume of 110 µL. Measurements were taken at a wavelength of 412 nm. All solutions were in MES Buffer (25 mM, pH 6.0). The kinetic activity of AAC(6')-li was first determined with varying concentrations of AcCoA and a fixed concentration of neamine, using the following solutions in 4 separate chambers: 1) MES buffer solution (25 mM); 2) various concentrations of AcCoA (50, 100, 150, and 200 µM); 3) neamine (1.6 mM) and DTNB (4 mM); and 4) AAC(6')-li (4 µM). The enzymatic activity of AAC(6')-li was next determined in the presence of the molecules of interest to measure inhibition constants ($K_i$). To this end, the following solutions were separated in the instrument into 4 chambers: 1) MES buffer solution (25 mM); 2) varying concentrations of inhibitor (1, 2, 4, and 8 µM) mixed with various concentrations of AcCoA (50, 100, 150, and 200 μM); 3) neamine (1.6 mM) and DTNB (4 mM); and 4) AAC(6')-li (4 μM). All data points are from triplicate experiments.

PanK enzyme assay. The *E. coli* pantothenate kinase (PanK or coaA enzyme) was expressed and purified as previously described. Enzyme activity was measured as described in the literature [Strauss E, Begley T P J Biol Chem, 2002, 277: 48205-48209]. This assay couples the production of ADP to the consumption of NADH through the activity of pyruvate kinase and lactic dehydrogenase. The decrease of NADH concentration was monitored at 340 nm. Reactions were performed at 25° C. in an Agilent 8453 UV-Vis spectrophotometer coupled to an Agilent 89090A Peltier temperature controller. Kinetic parameters were determined by fitting the rate data into the Michaelis-Menten equation using Prism 4.0 (GraphPad). Each reaction mixture (500 μL) contained ATP (1.5 mM), NADH (0.3 mM), phosphoenolpyruvate (0.5 mM), $MgCl_2$ (10 mM), KCl (20 mM), pyruvate kinase (5 units), lactic dehydrogenase (5 units), and PanK (5 μg, 278 nM) in Tris-HCl buffer (50 mM, pH 7.6). The reaction was initiated by addition of the desired substrate (10-160 μM). All data points are from triplicate experiments.

Biosynthetic in vitro assay with a mixture of PanK, PPAT and DPCK enzymes. The *E. coli* enzymes pantothenate kinase (PanK or coaA enzyme), phosphopantetheine adenylyltransferase (PPAT or coaD enzyme), and dephosphocoenzyme A kinase (DPCK or coaE enzyme) were expressed and purified as previously described [Geerlof A, Lewendon A, Shaw W V J Biol Chem 1999, 274:27105-27111]. Each reaction mixture (500 μL) contained ATP (5.0 mM), KCl (20 mM), $MgCl_2$ (10 mM), DTT (2.0 mM), PanK (5 μg, 278 nM), PPAT (5 μg, 500 nM), DPCK (5 μg, 454 nM) in Tris-Cl Buffer (50 mM, pH 7.6). The reaction was initiated with the addition of pantetheine (5.0 mM) for comparison, water as a negative control, or compounds 3a-e (5.0 mM). Reactions were incubated for 3 hours at room temperature and then stopped by heating the mixture to 95° C. for 5 min. The precipitated protein was removed by centrifugation (13,000 rpm for 5 min) and the supernatant was analyzed by LC/MS. Reversed-phase analytical HPLC was performed with an analytical 4.60×250 mm, SYNERGI 4p Hydro-RP 80A (Phenomenex, Torrance, Calif.) column coupled to an Agilent 6120 Quadrupole LC/MS system for ESI-MS analysis. The HPLC conditions had the sample eluted at a flow rate of 0.5 mL min$^{-1}$ using a combination of mobile phase A ($H_2O$) and mobile phase B (acetonitrile), Elution conditions are as follows: isocratic 1% phase B from 0-3 min; followed by the following linear gradients of phase B: 1-10% from 3-5 min; 10-15% from 5-10 min; 15-30% from 10-13 min; an finally isocratic phase B at 30% from 13-26 min. The detector was set to 214 nm. These experiments were run in duplicate.

Checkerboard assay to determine the synergistic activity of compounds 3a-f with kanamycin A or tobramycin on a resistant strain. A two dimensional checkerboard MIC assay was carried out as previously described [Gao F, Yan X, Shakya T, Baettig O M, Ait-Mohand-Brunet S, Berghuis A M, Wright G D, Auclair K; J Med Chem, 2006, 49:5273-5281] to observe for the potentiation activity of compounds 3a-f towards the antibacterial activity of kanamycin A or tobramycin against *Enterococcus faecium* ATCC 19434 which expresses AAC (6')-li naturally, or an *E. coli* strain engineered to express AAC(6)-li. Compounds 3a-f were diluted by 2-fold sequential dilutions to create a gradient from 32 to 512 μg/mL while the concentrations used for kanamycin A or tobramycin were 0, 10, 20, 40, 50, 100, 150, 200, 250, and 300 μg/mL. The cultures were grown at 37° C. for 16 h in 96-well plates, and then monitored for optical density at 600 nm using a Spectramax 190 microplate reader (Molecular Devices, Sunnyvale, Calif.). Data was normalized against a positive growth control and reported as a percentage of bacterial cell growth. All data points are from quadruplicate experiments.

Expression and purification of AAC(6')-li. AAC(6')-li was obtained using a previously described protocol [Wright G. D. and Ladak, P. Antimicrobial Agents and Chemotherapy, 1997, 41: 956-960]. The *Escherichia* coli strain BL21 was transformed with a pET22b expression plasmid containing the AAC(6')-li gene. The bacteria were grown in Luria-Bertani (LB) media at 37° C. containing ampicillin (100 μg/mL). Expression of the protein was induced using isopropyl-β-D-thiogalactoside (IPTG). After harvesting the cells by centrifugation and washing them with a 0.85% NaCl solution, the cells were lysed by sonication. AAC(6)-li was purified in a two-step process: firstly, the lysate was ran through a Q-Sepharose ion exchange column (GE Healthsciences), and secondly the AAC(6')-li containing fractions were further purified using a Gentamicin agarose affinity column (Bio-Rad).

While specific embodiments of the present invention have been described in the examples, it is apparent that modifications and adaptations of the present invention will occur to those skilled in the art. The embodiments of the present invention are not intended to be restricted by the examples. It is to be expressly understood that such modifications and adaptations which will occur to those skilled in the art are within the scope of the present invention, as set forth in the following claims. For instance, features illustrated or described as part of one embodiment can be used in another embodiment, to yield a still further embodiment. Thus, it is intended that the present invention cover such modifications and variations as come within the scope of the claims and their equivalents.

The contents of all documents and references cited herein are hereby incorporated by reference in their entirety.

The invention claimed is:
1. A compound of Formula 1A:

Formula 1A

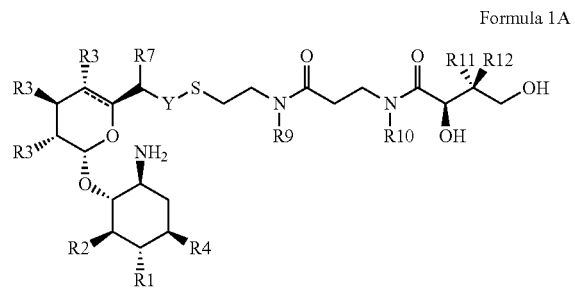

or a pharmaceutically acceptable salt thereof;
wherein
R1 is selected from the group consisting of OH

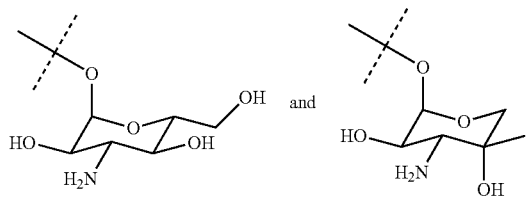

R2 is selected from the group consisting of OH and

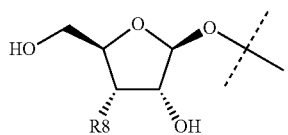

R3 is selected from the group consisting of H, $NH_2$ and OH;

R4 is selected from the group consisting of NH$_2$ and

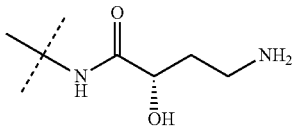

R7 is selected from the group consisting of H and CH$_3$;
R8 is selected from a group consisting of OH

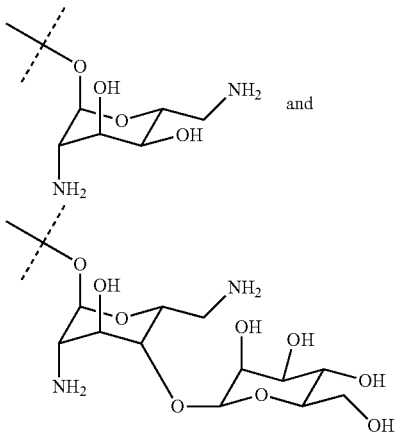

and

Y is

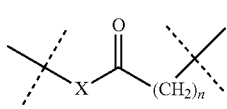

and X is NH,
R6 is selected from the group consisting of OH, CH$_3$, and OCH$_3$;
n is an integer from 2 to 5; and
R9, R10, R11 and R12 are each independently selected from the group consisting of H and C1-6 alkyl;
provided that when the dotted line is a double bond, R3 of the residue

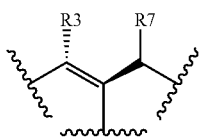

is H.

2. The compound of claim 1 or a pharmaceutically acceptable salt thereof, wherein R1 is OH and R2 is OH.

3. The compound of claim 1 or a pharmaceutically acceptable salt thereof, wherein R1 is OH and R2 is

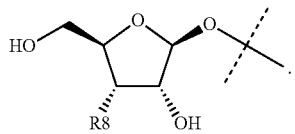

4. The compound of claim 3 or a pharmaceutically acceptable salt thereof, wherein R8 is OH.

5. The compound of claim 1 or a pharmaceutically acceptable salt thereof, wherein R1 is selected from the group consisting of

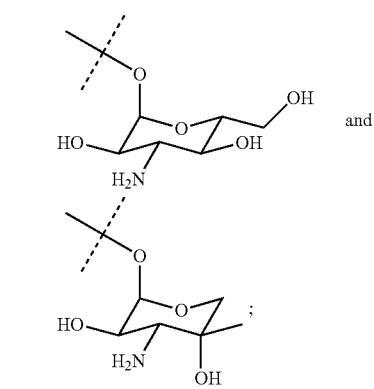

and R2 is OH.

6. The compound of claim 1 or a pharmaceutically acceptable salt thereof, wherein when one of R3 is NH$_2$, the others of R3 is OH or H.

7. The compound of claim 1 or a pharmaceutically acceptable salt thereof, wherein R7 is H.

8. The compound of claim 1 or a pharmaceutically acceptable salt thereof, wherein R4 is NH$_2$.

9. The compound of claim 1 or a pharmaceutically acceptable salt thereof, wherein R9 and R10 are each independently selected from the group consisting of H and C1-3 alkyl and R11 and R12 are each independently C1-3 alkyl.

10. The compound of claim 9 or a pharmaceutically acceptable salt thereof, wherein R9 and R10 are H.

11. The compound of claim 1 which is

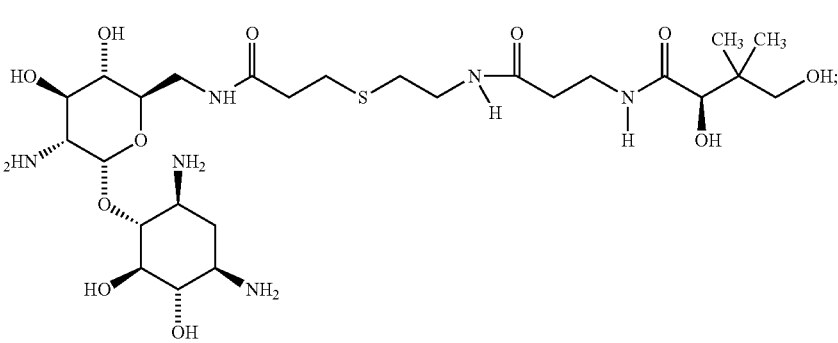

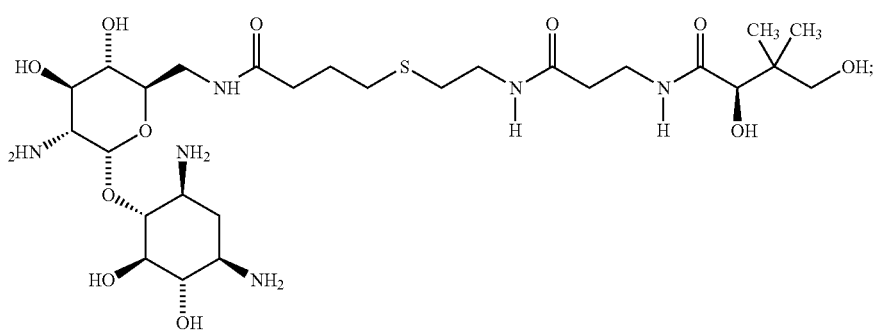
3c
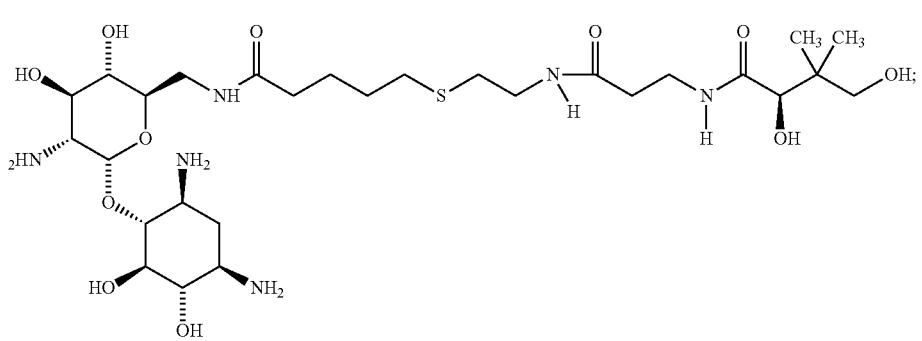
3d
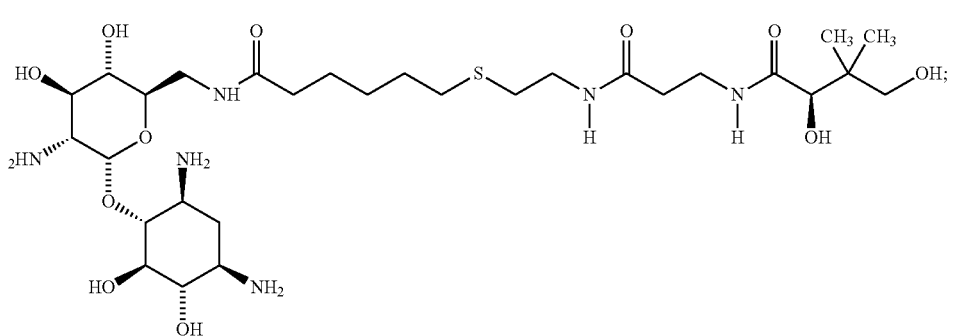
3e
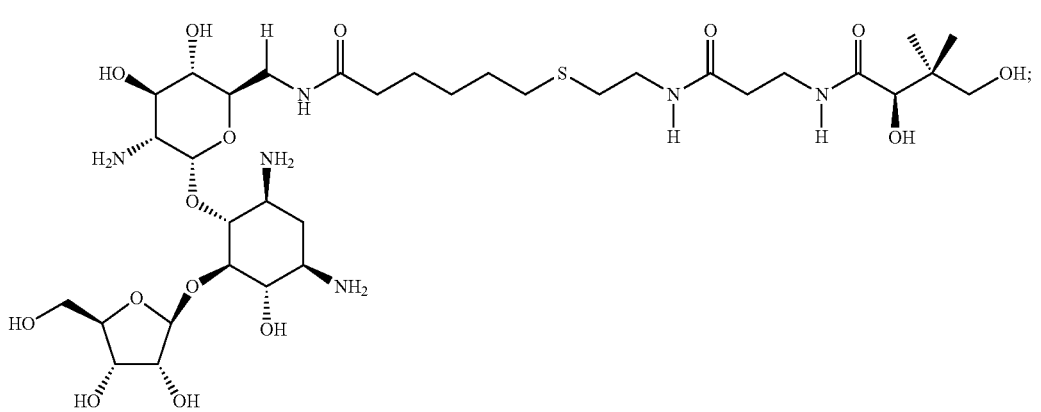
3f

-continued

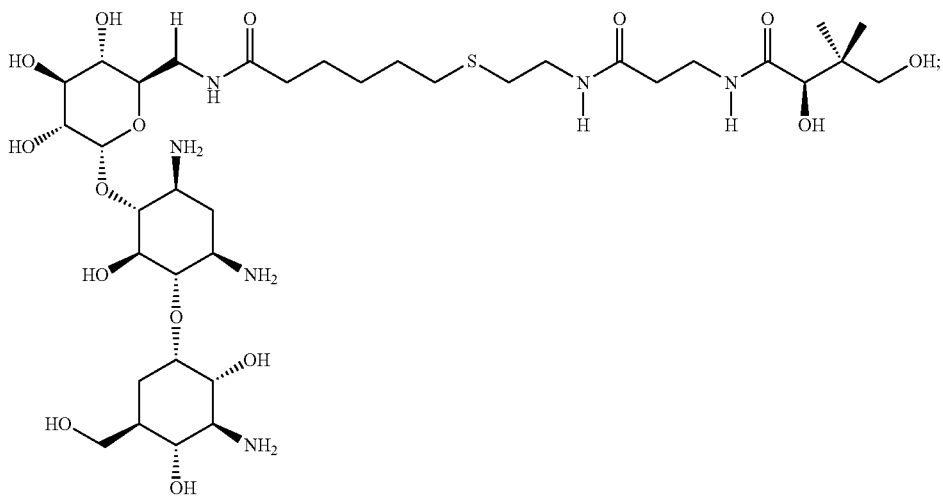

or a pharmaceutically acceptable salt thereof.

12. A method for reducing or reversing bacterial resistance to at least one aminoglycoside antibiotic comprising administering to a subject in need thereof, a compound as defined in claim 1 or a pharmaceutically acceptable salt thereof in an amount effective to cause a reduction or reversal of bacterial resistance to said at least one aminoglycoside antibiotic.

13. A pharmaceutical composition comprising at least one compound as defined in claim 1 or a pharmaceutically acceptable salt thereof, in association with one or more pharmaceutically acceptable carriers, excipients or diluents.

14. The pharmaceutical composition of claim 13 further comprising at least one aminoglycoside antibiotic.

15. The pharmaceutical composition of claim 14, wherein the aminoglycoside antibiotic is selected from the group consisting of amikacin, gentamicin; kanamycin; neomycin; netilmicin; streptomycin, tobramycin, ribostamycin, ciprofloxacin and trovafloxacin.

16. The method of claim 12 wherein said compound is

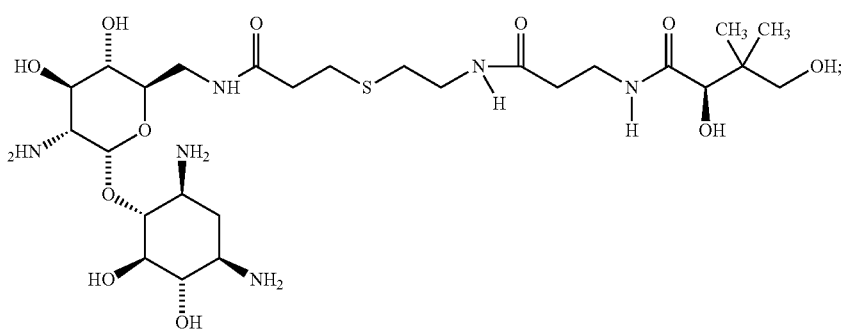

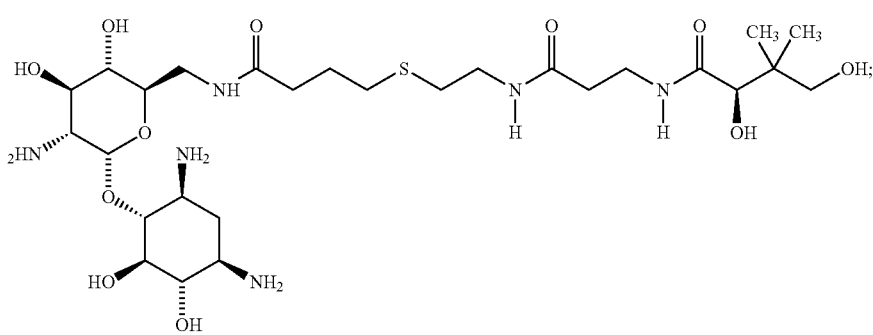

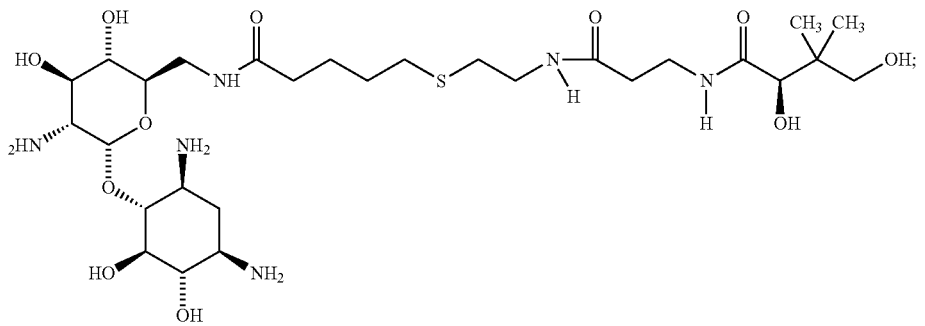
3d
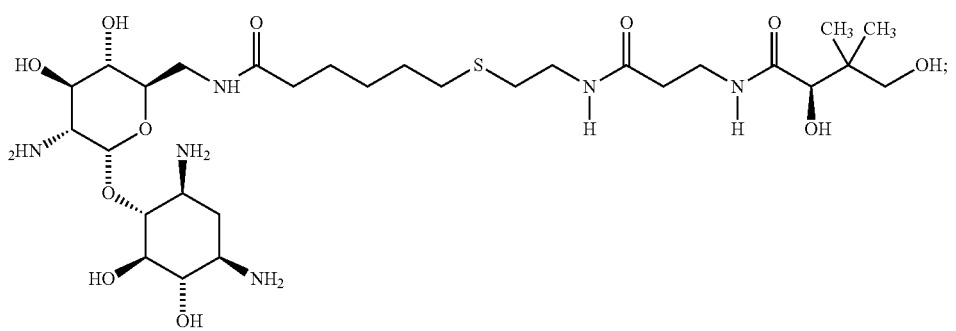
3e
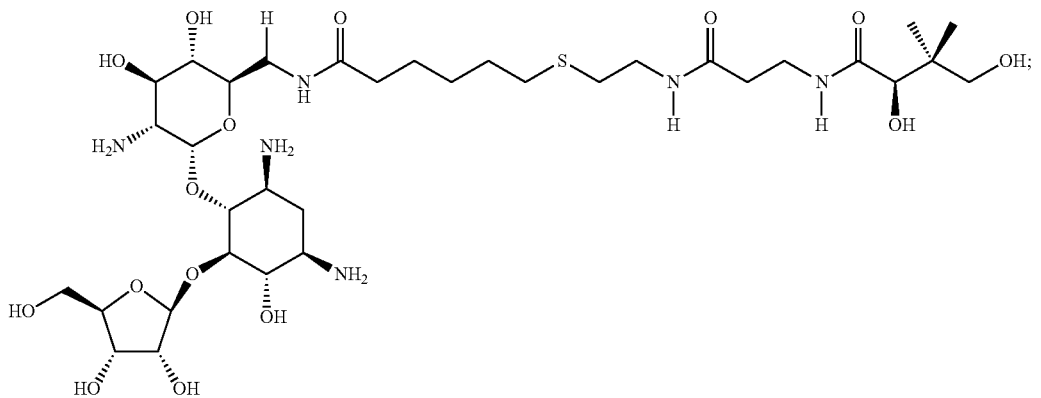
3f
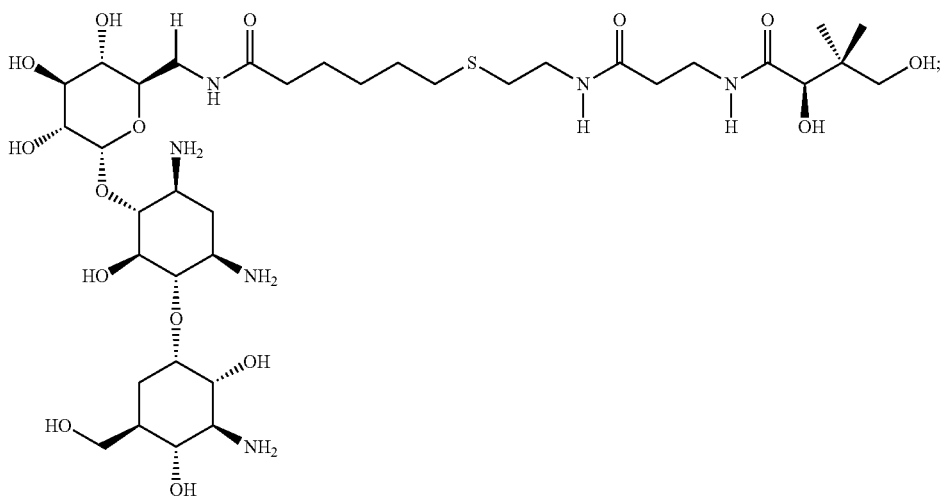
3g
or a pharmaceutically acceptable salt thereof.
* * * * *